(12) United States Patent
Kaplan et al.

(10) Patent No.: US 7,853,331 B2
(45) Date of Patent: Dec. 14, 2010

(54) MEDICAL DEVICE WITH PROCEDURE IMPROVEMENT FEATURES

(75) Inventors: Gary S. Kaplan, San Francisco, CA (US); Christopher J. Danek, San Carlos, CA (US); William J. Wizeman, Mountain View, CA (US); Tim R. Dalbec, Saratoga, CA (US)

(73) Assignee: Asthmatx, Inc., Sunnyvale, CA (US)

( * ) Notice: Subject to any disclaimer, the term of this patent is extended or adjusted under 35 U.S.C. 154(b) by 1153 days.

(21) Appl. No.: 11/420,442

(22) Filed: May 25, 2006

(65) Prior Publication Data

US 2006/0247619 A1 Nov. 2, 2006

Related U.S. Application Data

(63) Continuation of application No. PCT/US2005/040378, filed on Nov. 7, 2005.

(60) Provisional application No. 60/625,256, filed on Nov. 5, 2004, provisional application No. 60/650,368, filed on Feb. 4, 2005.

(51) Int. Cl.
*A61F 7/12* (2006.01)
(52) U.S. Cl. .............................. 607/99; 607/96; 607/98
(58) Field of Classification Search .................. 606/41, 606/42, 46–50; 607/101, 96, 98–102, 104–105 D
See application file for complete search history.

(56) References Cited

U.S. PATENT DOCUMENTS

| | | | |
|---|---|---|---|
| 1,155,169 A | 9/1915 | Starkweather |
| 1,207,479 A | 12/1916 | Bisgaard |
| 2,072,346 A | 3/1937 | Smith |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 4,461,283 A | 7/1984 | Doi |
| 4,503,855 A | 3/1985 | Maslanka |
| 4,522,212 A | 6/1985 | Gelinas et al. |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,643,186 A | 2/1987 | Rosen et al. |
| 4,674,497 A | 6/1987 | Ogasawara |
| 4,706,688 A | 11/1987 | Don Michael et al. |
| 4,709,698 A | 12/1987 | Johnston et al. |

(Continued)

FOREIGN PATENT DOCUMENTS

| | | |
|---|---|---|
| EP | 189329 A3 | 6/1987 |
| EP | 908713 A1 | 4/1999 |
| EP | 908150 B1 | 5/2003 |
| EP | 1297795 B1 | 8/2005 |
| FR | 2659240 B1 | 7/1997 |
| JP | 7289557 A2 | 11/1995 |
| RU | 2053814 C1 | 2/1996 |
| RU | 2091054 C1 | 9/1997 |
| WO | WO-8911311 A1 | 11/1989 |

(Continued)

OTHER PUBLICATIONS

Co-pending U.S. Appl. No. 09/244,173.

(Continued)

*Primary Examiner*—Roy D Gibson
(74) *Attorney, Agent, or Firm*—Perkins Coie LLP

(57) ABSTRACT

This relates to methods and devices for achieving contact between the wall of a cavity or passageway and a medical device under conditions in which an access path and the subject anatomy are not aligned.

10 Claims, 14 Drawing Sheets

U.S. PATENT DOCUMENTS

| | | |
|---|---|---|
| 4,799,479 A | 1/1989 | Spears |
| 4,802,492 A | 2/1989 | Grunstein |
| 4,825,871 A | 5/1989 | Cansell |
| 4,827,935 A | 5/1989 | Geddes et al. |
| 4,862,886 A | 9/1989 | Clarke et al. |
| 4,920,978 A | 5/1990 | Colvin |
| 4,955,377 A | 9/1990 | Lennox et al. |
| 4,967,765 A | 11/1990 | Turner et al. |
| 4,976,709 A | 12/1990 | Sand |
| 5,010,892 A | 4/1991 | Colvin et al. |
| 5,019,075 A | 5/1991 | Spears et al. |
| 5,053,033 A | 10/1991 | Clarke |
| 5,056,519 A | 10/1991 | Vince |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,106,360 A | 4/1992 | Ishiwara et al. |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,215,103 A | 6/1993 | Desai |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,311,866 A | 5/1994 | Kagan et al. |
| 5,313,943 A | 5/1994 | Houser et al. |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,394,880 A | 3/1995 | Atlee, III |
| 5,396,887 A | 3/1995 | Imran |
| 5,400,783 A | 3/1995 | Pomeranz et al. |
| 5,409,469 A | 4/1995 | Schaerf |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,423,744 A | 6/1995 | Gencheff et al. |
| 5,423,811 A | 6/1995 | Imran et al. |
| 5,425,703 A | 6/1995 | Feiring |
| 5,431,696 A | 7/1995 | Atlee, III |
| 5,433,730 A | 7/1995 | Alt |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,464,404 A | 11/1995 | Abela et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,500,011 A | 3/1996 | Desai |
| 5,505,728 A | 4/1996 | Ellman et al. |
| 5,505,730 A | 4/1996 | Edwards |
| 5,509,411 A | 4/1996 | Littmann et al. |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,562,619 A | 10/1996 | Mirarchi et al. |
| 5,571,088 A | 11/1996 | Lennox et al. |
| 5,578,067 A | 11/1996 | Ekwall et al. |
| 5,582,609 A | 12/1996 | Swanson et al. |
| 5,588,432 A | 12/1996 | Crowley |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,628,313 A * | 5/1997 | Webster, Jr. ................. 600/374 |
| 5,630,425 A | 5/1997 | Panescu et al. |
| 5,630,794 A | 5/1997 | Lax et al. |
| 5,634,471 A | 6/1997 | Fairfax et al. |
| 5,647,870 A | 7/1997 | Kordis et al. |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,693,078 A | 12/1997 | Desai et al. |
| 5,699,799 A | 12/1997 | Xu et al. |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,728,094 A | 3/1998 | Edwards |
| 5,730,128 A | 3/1998 | Pomeranz et al. |
| 5,730,726 A | 3/1998 | Klingenstein |
| 5,730,741 A | 3/1998 | Horzewski et al. |
| 5,740,808 A | 4/1998 | Panescu et al. |
| 5,752,518 A | 5/1998 | McGee et al. |
| 5,755,753 A | 5/1998 | Knowlton |
| 5,759,158 A | 6/1998 | Swanson |
| 5,769,846 A | 6/1998 | Edwards et al. |
| 5,772,590 A | 6/1998 | Webster, Jr. |
| 5,779,669 A | 7/1998 | Haissaguerre et al. |
| 5,779,698 A | 7/1998 | Clayman et al. |
| 5,782,239 A | 7/1998 | Webster, Jr. |
| 5,782,795 A | 7/1998 | Bays |
| 5,782,827 A | 7/1998 | Gough et al. |
| 5,782,899 A | 7/1998 | Imran |
| 5,792,064 A | 8/1998 | Panescu et al. |
| 5,795,303 A | 8/1998 | Swanson et al. |
| 5,807,306 A | 9/1998 | Shapland et al. |
| 5,810,807 A | 9/1998 | Ganz et al. |
| 5,814,029 A | 9/1998 | Hassett |

| | | | | | |
|---|---|---|---|---|---|
| 5,823,189 A | 10/1998 | Kordis | 6,039,731 A | 3/2000 | Taylor et al. |
| 5,824,359 A | 10/1998 | Khan et al. | 6,045,549 A | 4/2000 | Smethers et al. |
| 5,827,277 A | 10/1998 | Edwards | 6,045,550 A | 4/2000 | Simpson et al. |
| 5,833,632 A | 11/1998 | Jacobsen et al. | 6,050,992 A | 4/2000 | Nichols |
| 5,836,946 A | 11/1998 | Diaz et al. | 6,053,172 A | 4/2000 | Hovda et al. |
| 5,836,947 A | 11/1998 | Fleischman et al. | 6,056,744 A | 5/2000 | Edwards |
| 5,837,001 A | 11/1998 | Mackey | 6,056,769 A | 5/2000 | Epstein et al. |
| 5,843,075 A | 12/1998 | Taylor | 6,066,132 A | 5/2000 | Chen et al. |
| 5,843,077 A | 12/1998 | Edwards | 6,071,279 A | 6/2000 | Whayne et al. |
| 5,846,238 A | 12/1998 | Jackson et al. | 6,071,280 A | 6/2000 | Edwards et al. |
| 5,848,969 A | 12/1998 | Panescu et al. | 6,071,281 A | 6/2000 | Burnside et al. |
| 5,848,972 A | 12/1998 | Triedman et al. | 6,071,282 A | 6/2000 | Fleischman |
| 5,855,577 A | 1/1999 | Murphy-Chutorian et al. | 6,083,255 A | 7/2000 | Laufer et al. |
| 5,860,974 A | 1/1999 | Abele | 6,092,528 A | 7/2000 | Edwards |
| 5,863,291 A | 1/1999 | Schaer | 6,102,886 A | 8/2000 | Lundquist et al. |
| 5,865,791 A | 2/1999 | Whayne et al. | 6,119,030 A | 9/2000 | Morency |
| 5,868,740 A | 2/1999 | LeVeen et al. | 6,123,703 A | 9/2000 | Tu et al. |
| 5,871,443 A | 2/1999 | Edwards et al. | H1905 H | 10/2000 | Hill |
| 5,871,523 A | 2/1999 | Fleischman et al. | 6,129,751 A | 10/2000 | Lucchesi et al. |
| 5,873,865 A | 2/1999 | Horzewski et al. | 6,139,527 A | 10/2000 | Laufer et al. |
| 5,876,340 A | 3/1999 | Tu et al. | 6,142,993 A | 11/2000 | Whayne et al. |
| 5,876,399 A | 3/1999 | Chia et al. | 6,143,013 A | 11/2000 | Samson et al. |
| 5,881,727 A | 3/1999 | Edwards | 6,149,647 A | 11/2000 | Tu et al. |
| 5,882,346 A | 3/1999 | Pomeranz et al. | 6,152,899 A | 11/2000 | Farley et al. |
| 5,891,135 A | 4/1999 | Jackson et al. | 6,159,194 A | 12/2000 | Eggers et al. |
| 5,891,136 A | 4/1999 | McGee et al. | 6,179,833 B1 | 1/2001 | Taylor |
| 5,891,138 A | 4/1999 | Tu et al. | 6,183,468 B1 | 2/2001 | Swanson et al. |
| 5,893,847 A | 4/1999 | Kordis | 6,198,970 B1 | 3/2001 | Freed et al. |
| 5,897,554 A | 4/1999 | Chia et al. | 6,200,311 B1 | 3/2001 | Danek et al. |
| 5,899,882 A | 5/1999 | Waksman et al. | 6,200,332 B1 | 3/2001 | Del Giglio |
| 5,904,651 A | 5/1999 | Swanson et al. | 6,200,333 B1 | 3/2001 | Laufer |
| 5,904,711 A | 5/1999 | Flom et al. | 6,210,367 B1 | 4/2001 | Carr |
| 5,906,636 A | 5/1999 | Casscells, III et al. | 6,214,002 B1 | 4/2001 | Fleischman et al. |
| 5,908,445 A | 6/1999 | Whayne et al. | 6,216,043 B1 | 4/2001 | Swanson et al. |
| 5,908,446 A | 6/1999 | Imran | 6,216,044 B1 | 4/2001 | Kordis |
| 5,911,218 A | 6/1999 | DiMarco | 6,217,576 B1 | 4/2001 | Tu et al. |
| 5,916,235 A | 6/1999 | Guglielmi | 6,235,024 B1 | 5/2001 | Tu |
| 5,919,147 A | 7/1999 | Jain | 6,241,727 B1 | 6/2001 | Tu et al. |
| 5,921,999 A | 7/1999 | Dileo | 6,251,104 B1 | 6/2001 | Kesten et al. |
| 5,928,228 A | 7/1999 | Kordis et al. | 6,254,598 B1 | 7/2001 | Edwards et al. |
| 5,935,079 A | 8/1999 | Swanson et al. | 6,258,083 B1 * | 7/2001 | Daniel et al. .................. 606/15 |
| 5,941,869 A | 8/1999 | Patterson et al. | 6,258,087 B1 | 7/2001 | Edwards et al. |
| 5,951,494 A | 9/1999 | Wang et al. | 6,270,476 B1 | 8/2001 | Santoianni et al. |
| 5,954,661 A | 9/1999 | Greenspon et al. | 6,273,907 B1 | 8/2001 | Laufer |
| 5,954,662 A | 9/1999 | Swanson et al. | 6,283,988 B1 | 9/2001 | Laufer et al. |
| 5,954,717 A | 9/1999 | Behl et al. | 6,283,989 B1 | 9/2001 | Laufer et al. |
| 5,957,842 A | 9/1999 | Littmann et al. | 6,296,639 B1 | 10/2001 | Truckai et al. |
| 5,957,961 A | 9/1999 | Maguire et al. | 6,299,633 B1 | 10/2001 | Laufer |
| 5,964,753 A | 10/1999 | Edwards | 6,322,559 B1 | 11/2001 | Daulton et al. |
| 5,964,796 A | 10/1999 | Imran | 6,322,584 B2 | 11/2001 | Ingle et al. |
| 5,968,087 A | 10/1999 | Hess et al. | 6,338,727 B1 | 1/2002 | Noda et al. |
| 5,971,983 A | 10/1999 | Lesh | 6,338,836 B1 | 1/2002 | Kuth et al. |
| 5,972,026 A | 10/1999 | Laufer et al. | 6,379,352 B1 | 4/2002 | Reynolds et al. |
| 5,979,456 A | 11/1999 | Magovern | 6,409,723 B1 | 6/2002 | Edwards |
| 5,980,563 A | 11/1999 | Tu et al. | 6,411,852 B1 | 6/2002 | Danek et al. |
| 5,991,650 A | 11/1999 | Swanson et al. | 6,416,511 B1 | 7/2002 | Lesh et al. |
| 5,992,419 A | 11/1999 | Sterzer et al. | 6,423,105 B1 | 7/2002 | Iijima et al. |
| 5,993,462 A | 11/1999 | Pomeranz et al. | 6,425,895 B1 | 7/2002 | Swanson et al. |
| 5,997,534 A | 12/1999 | Tu et al. | 6,440,129 B1 | 8/2002 | Simpson |
| 5,999,855 A | 12/1999 | DiMarco | 6,442,435 B2 | 8/2002 | King et al. |
| 6,003,517 A | 12/1999 | Sheffield et al. | 6,460,545 B2 | 10/2002 | Kordis |
| 6,004,269 A | 12/1999 | Crowley et al. | 6,488,673 B1 | 12/2002 | Laufer et al. |
| 6,006,755 A | 12/1999 | Edwards | 6,493,589 B1 | 12/2002 | Medhkour et al. |
| 6,009,877 A | 1/2000 | Edwards | 6,496,738 B2 | 12/2002 | Carr |
| 6,010,500 A | 1/2000 | Sherman et al. | 6,514,246 B1 | 2/2003 | Swanson et al. |
| 6,014,579 A | 1/2000 | Pomeranz et al. | 6,526,320 B2 | 2/2003 | Mitchell |
| 6,016,437 A | 1/2000 | Tu et al. | 6,529,756 B1 | 3/2003 | Phan et al. |
| 6,023,638 A | 2/2000 | Swanson | 6,544,226 B1 | 4/2003 | Gaiser et al. |
| 6,024,740 A | 2/2000 | Lesh et al. | 6,544,262 B2 | 4/2003 | Fleischman |
| 6,029,091 A | 2/2000 | De La Rama et al. | 6,547,788 B1 | 4/2003 | Maguire et al. |
| 6,033,397 A | 3/2000 | Laufer et al. | 6,572,612 B2 | 6/2003 | Stewart et al. |
| 6,036,687 A | 3/2000 | Laufer et al. | 6,575,623 B2 | 6/2003 | Werneth |
| 6,036,689 A | 3/2000 | Tu et al. | 6,582,427 B1 | 6/2003 | Goble et al. |

| Patent Number | Date | Inventor |
|---|---|---|
| 6,582,430 B2 | 6/2003 | Hall |
| 6,589,235 B2 | 7/2003 | Wong et al. |
| 6,610,054 B1 | 8/2003 | Edwards et al. |
| 6,620,159 B2 | 9/2003 | Hegde |
| 6,626,903 B2 | 9/2003 | McGuckin, Jr. et al. |
| 6,634,363 B1 | 10/2003 | Danek et al. |
| 6,638,273 B1 | 10/2003 | Farley et al. |
| 6,640,120 B1 | 10/2003 | Swanson et al. |
| 6,645,199 B1 | 11/2003 | Jenkins et al. |
| 6,645,200 B1 | 11/2003 | Koblish et al. |
| 6,652,548 B2 | 11/2003 | Evans et al. |
| 6,669,693 B2 | 12/2003 | Friedman |
| 6,673,068 B1 | 1/2004 | Berube |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,749,607 B2 | 6/2004 | Edwards et al. |
| 6,767,347 B2 | 7/2004 | Sharkey et al. |
| 6,770,070 B1 | 8/2004 | Balbierz |
| 6,802,843 B2 | 10/2004 | Truckai et al. |
| 6,805,131 B2 | 10/2004 | Kordis |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,869,437 B1 | 3/2005 | Hausen et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,954,977 B2 | 10/2005 | Maguire et al. |
| 6,976,991 B2 * | 12/2005 | Hebert et al. ............... 606/194 |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,118,568 B2 | 10/2006 | Hassett et al. |
| 7,122,033 B2 | 10/2006 | Wood |
| 7,186,251 B2 | 3/2007 | Malecki et al. |
| 7,198,635 B2 | 4/2007 | Danek et al. |
| 7,200,445 B1 | 4/2007 | Dalbec et al. |
| 7,264,002 B2 | 9/2007 | Danek et al. |
| 7,273,055 B2 | 9/2007 | Danek et al. |
| 7,425,212 B1 | 9/2008 | Danek et al. |
| 7,556,624 B2 | 7/2009 | Laufer et al. |
| 2002/0072737 A1 | 6/2002 | Belden et al. |
| 2002/0091379 A1 | 7/2002 | Danek et al. |
| 2002/0147391 A1 | 10/2002 | Morency |
| 2002/0173785 A1 | 11/2002 | Spear et al. |
| 2003/0050631 A1 | 3/2003 | Mody et al. |
| 2003/0065398 A1 | 4/2003 | Satake |
| 2004/0031494 A1 | 2/2004 | Danek et al. |
| 2004/0153056 A1 | 8/2004 | Muller et al. |
| 2004/0182399 A1 | 9/2004 | Danek et al. |
| 2004/0249401 A1 | 12/2004 | Rabiner et al. |
| 2005/0010270 A1 | 1/2005 | Laufer |
| 2005/0096644 A1 | 5/2005 | Hall et al. |
| 2005/0154386 A1 | 7/2005 | West et al. |
| 2005/0182431 A1 | 8/2005 | Hausen et al. |
| 2005/0203503 A1 | 9/2005 | Edwards et al. |
| 2005/0240176 A1 | 10/2005 | Oral et al. |
| 2006/0062808 A1 | 3/2006 | Laufer et al. |
| 2006/0089637 A1 | 4/2006 | Werneth et al. |
| 2006/0135953 A1 | 6/2006 | Kania et al. |
| 2006/0247617 A1 | 11/2006 | Danek et al. |
| 2006/0247618 A1 | 11/2006 | Kaplan et al. |
| 2007/0100390 A1 | 5/2007 | Danaek et al. |
| 2007/0106292 A1 | 5/2007 | Kaplan et al. |
| 2007/0106296 A1 | 5/2007 | Laufer et al. |
| 2007/0118184 A1 | 5/2007 | Danek et al. |
| 2007/0123958 A1 | 5/2007 | Laufer |
| 2007/0123961 A1 | 5/2007 | Danek et al. |
| 2008/0097424 A1 | 4/2008 | Wizeman et al. |
| 2009/0018538 A1 | 1/2009 | Webster et al. |
| 2009/0043301 A1 | 2/2009 | Jarrard et al. |
| 2009/0069797 A1 | 3/2009 | Danek et al. |

FOREIGN PATENT DOCUMENTS

| | | |
|---|---|---|
| WO | WO-9304734 A1 | 3/1993 |
| WO | WO-9502370 A3 | 1/1995 |
| WO | WO-9510322 A1 | 4/1995 |
| WO | WO-9604860 A1 | 2/1996 |
| WO | WO-9610961 A1 | 4/1996 |
| WO | WO-9732532 A1 | 9/1997 |
| WO | WO-9733715 A1 | 9/1997 |
| WO | WO-9737715 A1 | 10/1997 |
| WO | WO-9844854 A1 | 10/1998 |
| WO | WO-9852480 A1 | 11/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO-9934741 A1 | 7/1999 |
| WO | WO-9944506 A1 | 9/1999 |
| WO | WO-9945855 A1 | 9/1999 |
| WO | WO-0051510 A1 | 9/2000 |
| WO | WO-0103642 A1 | 1/2001 |

OTHER PUBLICATIONS

Co-pending U.S. Appl. No. 09/095,323.

Simon R. Johnson et al., Synthetic Functions of Airway Smooth Muscle in Asthma, Trends Pharmacol. Sci., Aug. 1997, 18(8), 288-292.

Macklem P.T., Mechanical Factors Determining Maximum Bronchoconstriction, European Respiratory Journal, Jun. 1989, 6, 516s-519s.

James C. Hogg, The Pathology of Asthma, APMIS, Oct. 1997, 105(10), 735-745.

Dierkesmann et al., Indication and Results of Endobronchial Laser Therapy, Lung, 1990, 168, 1095-1102.

Netter F.H, Respiratory System: A Compilation of Paintings Depicting Anatomy and Embryology, Physiology, Pathology, Pathophysiology, and Clinical Features and Treatment of Diseases, in The CIBA Collection of Medical Illustrations M.B. Divertie, ed., Summit: New Jerse, 1979, vol. 7, 119-135.

Provotorov et al., The Clinical Efficacy of Treating Patients with Nonspecific Lung Disease by Using Low-energy Laser Irradiation and Intrapulmonary Drug Administration, ISSN: 0040-3660., Terapevticheskii Arkhiv (USSR), 1991, 63 (12), 18-23.

Vorotnev et al., Low energy laser treatment of chronic obstructive bronchitis in a general rehabilitation center, ISSN: 0040-3660., Terapevticheskii Arkhiv, 1997, 69 (3), 17-19.

Wiggs B.R. et al., On the Mechanism of Mucosal Folding in Normal and Asthmatic Airways, J. Appl. Physiol., Dec. 1997, 83(6), 1814-1821.

Ivaniuta O. M. et al., Effect Of Low-Power Laser Irradiation Of Bronchial Mucosa On The State Of Systemic And Local Immunity in Patients With Chronic Bronchitis, Problemy Tuberkuleza, 1991, 6, 26-29.

Co-pending U.S. Appl. No. 12/640,644, filed Dec. 17, 2009, Inventor Jerry Jarrard.

PCT International search report for application No. PCT/US05/40378 mailed on Aug. 8, 2006, 2 pages.

* cited by examiner

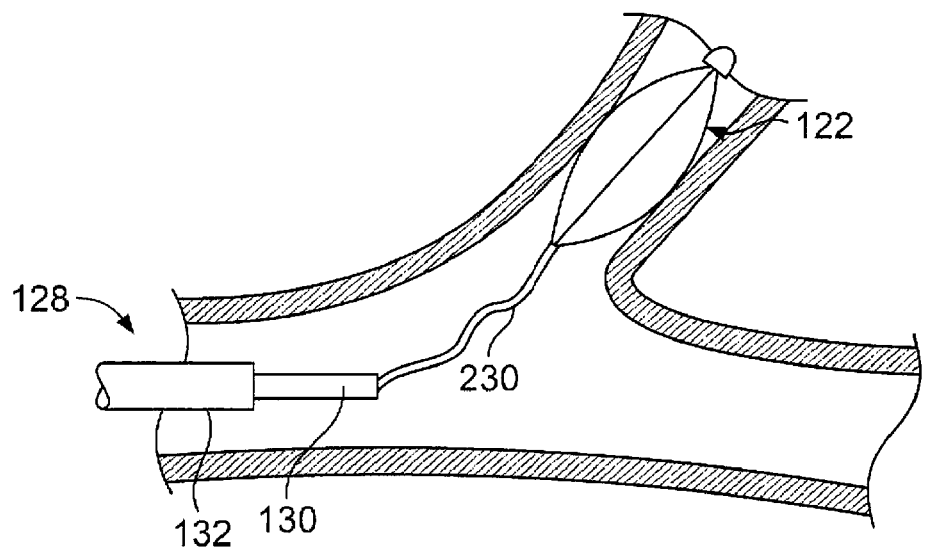
FIG. 7
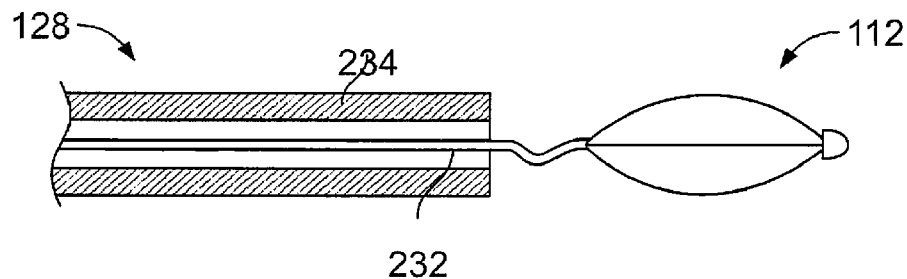
FIG. 8A
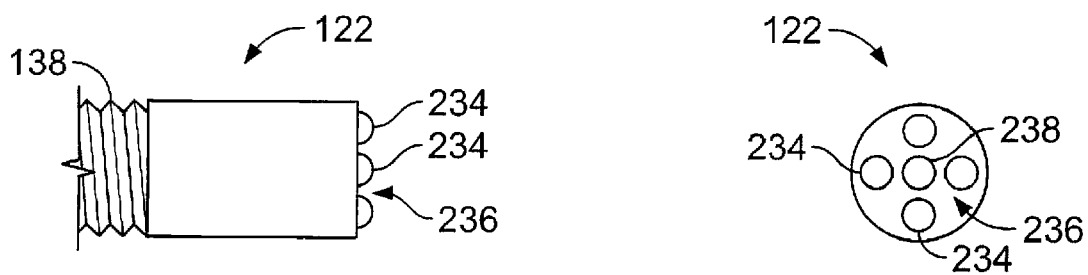
FIG. 9A  FIG. 9B

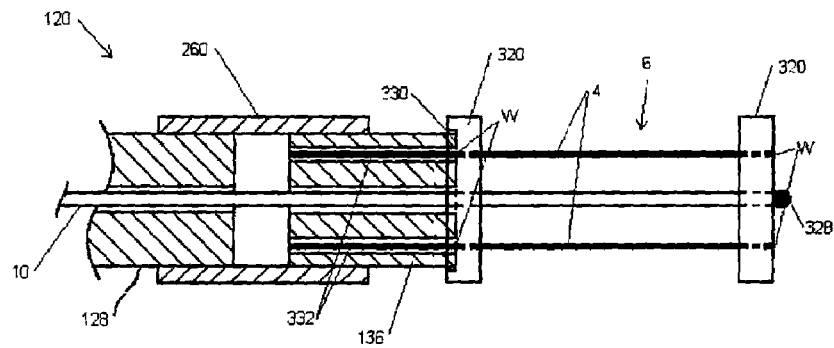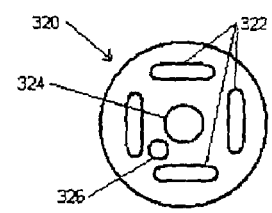
Fig. 15A    Fig. 15B
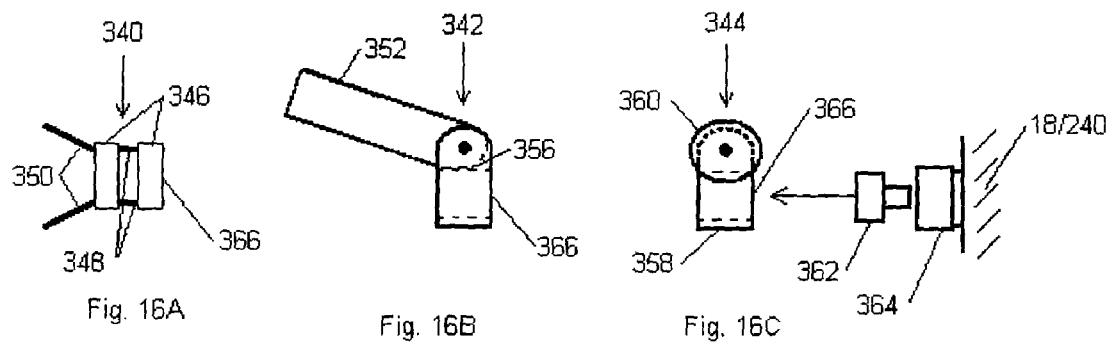
Fig. 16A    Fig. 16B    Fig. 16C

MEDICAL DEVICE WITH PROCEDURE IMPROVEMENT FEATURES

CROSS-REFERENCE TO RELATED APPLICATION

This application is a continuation of PCT Application Number PCT/US2005/040378, filed Nov. 7, 2005, which claims the benefit of U.S. Provisional Patent Application No. 60/625,256, filed Nov. 5, 2004 and U.S. Provisional Patent Application No. 60/650,368, filed Feb. 4, 2005, the contents of which are incorporated herein in their entirety.

BACKGROUND OF THE INVENTION

It is well understood that "minimally invasive" as opposed to open surgical approaches often offer benefits in terms of decreased patient trauma, increased patient acceptance, improved recuperation time, and lower associated costs—both monetarily and in terms of other metrics. Accordingly, instances of minimally invasive procedures are increasingly common.

However, in any case where a medical practitioner advances a device to a remote operative site (e.g., open surgical procedure with a remote operative site, percutaneous access, and/or access via an open body conduit) alignment or orientation difficulties with the subject device may arise. For example, various parts of the anatomy may create a situation where the access path is offset from the treatment site. Such examples include the tortuosity of the vasculature, turns of the colon, regions of the stomach not in direct alignment with the path of the esophagus, and the branching of bronchi.

Tortuous anatomy may also create challenges when the particular treatment device requires mechanical actuation of the treatment portion. In particular, attempting to actuate a member may be difficult if the actuation force applied at the operator's hand-piece must translate to the distal end of the device.

In addition to basic considerations of navigation and site access, there exists the matter of device orientation at the treatment site. Many treatment devices make contact or are placed in close proximity to the target tissue. Yet, if the access path is misaligned from the treatment site, then difficulties may arise in attempting to and achieve uniform contact (or near contact) at the desired treatment site.

As one example, commonly assigned U.S. Pat. No. 6,411,852, incorporated by reference herein, describes a device having flexible electrode members that can be expanded to better fill a space (e.g., the lumen of an airway.) However, the tortuous nature of the airways may cause significant bending and/or flexure of the distal end of the device. The flexure may impose non-uniform forces on the flexible electrode as a result of the airway wall. These non-uniform forces may result in distortion of one or more of the flexible electrodes. Aside from the possibility of damaging the device, distortion of the device may impact the treatment.

For many treatment devices, the distortion of the energy transfer elements might cause variability in the treatment effect. For example, many RF devices heat tissue based on the tissue's resistive properties. Increasing or decreasing the surface contact between the electrode and tissue, often increases or decreases the amount of current flowing through the tissue at the point of contact. This directly affects the amount of heat in the tissue. Similar concerns may also arise with resistive heating elements, "cold" devices, or any energy transfer device. In any number of cases, variability of the energy transfer/tissue interface causes variability in treatment results. The consequential risks range from an ineffective treatment to the possibility of patient injury.

Furthermore, most medical practitioners recognize the importance of establishing acceptable contact between the transfer element and tissue. Therefore, distortion of the transfer element or elements increases the procedure time when the practitioner spends an inordinate amount of time adjusting a device to compensate for or avoid such distortion. Such action becomes increasingly problematic in those cases where proper patient management limits the time available for the procedure.

For example, if a patient requires an increasing amount of medication (e.g., sedatives or anesthesia) to remain under continued control for performance of the procedure, then a medical practitioner may limit the procedure time rather than risk overmedicating the patient. As a result, rather than treating the patient continuously to complete the procedure, the practitioner may plan to break the procedure in two or more sessions. Subsequently, increasing the number of sessions poses additional consequences on the part of the patient in cost, the residual effects of any medication, etc.

SUMMARY OF THE INVENTION

The present invention includes devices configured to treat the airways or other anatomical structures (including those noted herein) with uniform or predictable contact (or near contact) between an active element and tissue. Typically, the invention allows this result with little or no effort by a physician. Accordingly, aspects of the invention offer increased effectiveness and efficiency in carrying out a medical procedure. The increases in effectiveness and efficiency may be especially apparent in using devices having relatively longer active end members.

Accordingly, a variation of the invention includes medical devices having an elongated member with an active distal end, and a junction between the two structures. The junction permits adjustment (e.g., angular, rotational, axial, etc.) of the active end relative to the elongate member in order to better position the active end to contact the tissue when the access pathway is not in alignment with the tissue.

A variation of the invention includes a device having a junction comprising a joint or flexure such as a living hinge or other element with sufficient column strength to allow navigation of the device with or without a supporting member. Exemplary structures include polymeric plugs, springs, various types of joints, struts, cutouts, sleeves, ball joints, etc. In additional variations, the joint itself may not have sufficient column strength and requires additional support (e.g., an external sheath or internal shaft) so that it may be navigated to the site. Examples of junctions of this nature include links, tethers, cables, braided or polymeric tubes, etc.

The active element of the device may have any number of elements in any particular configuration. In one variation, the active member may comprise an energy transfer element. In one example the active member may be in the form of a basket, individual expandable arms, a balloon or another structure carrying electrodes. Accordingly, the active member may be used for energy transfer (to or from tissue) to effect a change in the tissue structure. Alternatively, or in combination, the active member may map or provide information regarding the tissue site.

Other potential active member or distal end structures include a shell with opening for delivering cryogenic fluid (i.e., gas or liquid) or a chemical composition, and those presented in the '852 patent, each variation incorporated by reference herein—as well as the entire text of the subject documents.

Naturally, other junctions and active members may fall within the scope of the present invention. In addition, it is understood that methods in which device adjustment or realignment allows for improved active member orientation or placement over known devices or procedures forms part of the present invention. Such methods are advantageously practiced with the subject devices. The present invention also includes tuning the stiffness of the joint or junction such that in certain variations that the structure is not simply floppy, but rather bends or flexes to accommodate anatomy only or just before significant deformation of the one or more portions of the active member employed.

These methods are advantageously practiced in the bronchi, especially for the treatment of asthma. However, the invention is not limited to use in the lungs. The invention may be used in various parts of the body having tortuous anatomy or where the path to reach the target site is offset or misaligned from the target site. The invention is also suited for use in those environments where the target site undergoes motion (such as the tidal motion that accompanies breathing, the beating of the heart, etc.) In these cases, the junction absorbs or compensates for the motion at the target site. For example, when the energy transfer portion of the device secures to the target site, the junction allows the energy transfer portion to move with the target tissue.

Another variation of the invention includes a treatment system in which the minimally invasive access device such as an endoscope or similar device is configured to minimize misalignment as described herein. For example, many access devices, such as bronchoscope, typically include an offset working channel (where the working channel is the lumen through which a medical device may be advanced through the device). Usually, the working channel is offset to maximize its diameter while accommodating other channels (such as a lumen for aspiration and a lumen for visualization.) In the system of the present invention, the working lumen is centrally located to avoid the unpredictable effect created by offsetting the channel. The methods involving use of such a device resemble those carried out before, except they are performed without introducing misalignments by virtue of device orientation. It should be noted that any discussions of a scope or endoscope are intended to include the endoscope, bronchoscope, colonoscope, duodenoscope, and any other scope type device able to functionally provide medical device access.

Other modifications of a bronchoscope or one of the referenced devices may also be made according to the present invention. Specifically, surface modifications are contemplated to reduce friction or surface tension with fluid between the bronchoscope and a treatment device received therein. To do so, the working lumen of the bronchoscope (or other medical access device) may include a roughened, ribbed, striated, spiraling, scalloped, polygonal, or otherwise interrupted surface. Alternatively, the body of the treatment device may be so-configured. However employed, this aspect of the invention offers contact area surface reduction between the respective members.

With reduced surface contact, reduced friction/contact wear has been experienced relative to devices with unmodified (i.e., substantially smooth) interface surfaces. A useful characteristic of a system with decreased frictional or surface tension forces is that an elongate body of the treatment device will experience less compression upon advancement within the bronchoscope. Less compression, in turn, results in a decreased tendency for the active end of the device to jump or jut forward as compression is released. As such, the system may be more atraumatic or offer benefits in terms of accurate active member placement.

Similar benefits can be achieved within the treatment catheter itself. Specifically, in cases where the treatment device includes a actuation wire to manipulate its active end, the wire or the lumen through which the wire passes may be textured, striated, ribbed, undercut, polygonal, etc. as above. Using braiding or twisted cable for the "wire" may offer a particularly elegant solution in regard to reducing contact forces within the treatment catheter body.

In any of the immediately preceding aspects of the invention, material selection and coatings may alternatively or additionally be applied to reduce friction or surface tension effects between moving members. Hydrophilic coatings and other low-friction polymer material such as PTFE (as a coating or a material layer for body construction) may be employed for such purposes. Note, however, that experience by the inventors hereof with each of optimizing material selection and altering geometry to reduce surface contact has shown that the geometry change may be more beneficial. Still, either one or both approaches may be employed to improve device performance.

Device performance can also be improved to offer consistent bending characteristics. Known treatment catheters as referenced herein typically include a pair of lumen therethrough. A central lumen is provided for the actuation wire, and a second offset lumen is provided for a thermocouple wire. According to one aspect of the invention, a symmetrical body lumen design is adopted instead of known asymmetrical approaches. Stated otherwise, the cross-section is balanced to include complimentary holes or spaces. As few as two, preferably, crescent-shaped holes may be provided centered about the wire lumen in the body. Alternatively, sets of three, four or more holes of oval, circular or another configuration will be provided around the circumference of the treatment device body to improve symmetry in its bending performance.

Yet another option involves providing symmetrically located channels, grooves, etc. in the wall of the catheter body around its circumference. In fact, a combination of approaches may be taken. Any arrangement (especially of repeating symmetrical units) that produces a more even flex profile (or consistent moment of inertia about multiple axes perpendicular to a linear axis of the catheter body) may be employed according to this aspect of the invention.

When removing material in a design as described above it may, however, be important to balance other considerations. Namely, the treatment catheter should have sufficient column strength so as to be pushable for advancement to a treatment site. The required stiffness or column strength will typically depend on the application.

Another aspect of the invention recognizes that it is possible to maintain the column strength of the catheter while altering (i.e., improving) the flex characteristics by symmetrical removal of material. As known, the cross-sectional area of a body determines the column strength. Therefore, desirable column strength can be retained by increasing the diameter of the catheter body in order to maintain its cross-sectional area. Further, since the area of a circular cross section is a function of its radius squared, then it may not be necessary to add much size to the diameter of the catheter body to provide desired pushability while optimizing its flex properties.

Another aspect of the invention involves improving the construction of the active member of the treatment device. One or two construction collars may be used in assembling a basket type structure from a plurality of wire or metal ribbon pieces. The collars will be located on either or both ends of the basket. Especially when two are used, they offer a means of precision alignment and orientation for assembly of the other device pieces. Furthermore, even without the need to measure-out the length of individual segments, the collars help define an active member structure with even length arms/legs. Each of these factors help in producing devices with improved or more predictable actuation.

Another aspect of the invention involves the manner in which the wire or ribbon segments of the basket are attached to the collar(s). Specifically, when welded, the location for the weld joint(s) is to the exterior of the collar. This way, sections of the arms/legs of the basket that are highly stressed in bending inside of the collar(s) do not loose strength from annealing by the heat of welding.

Still other aspects of the invention are directed toward improving ease of system use. One such feature is a device locator or lock. As a locator, gradations or a scale marking location along the body of the treatment device, or a stop fixing ultimate insertion depth within an access device may be employed. As a lock, fittings (e.g. leur fittings), clips, clamps, etc. may be employed. When a lock or stop is employed, it may be located on the treatment catheter body at a location corresponding to the desired insertion depth within the access device (e.g., bronchoscope) employed. When a scale or gradations on the body of the treatment catheter are provided, these provide a visual indication of either the length of insertion of the treatment catheter, the portion of the device distal the end of a know-length access device, or some other measurement to assist in setting the position of the distal end of the treatment catheter relative to the end of the access device/bronchoscope.

In another variation of the invention, a clamp, clip or another type of locking member can be provided in connection with or integral with the access device. With the lock set on the access device and secured to the treatment device, the lock will simply hold the devices together once an operator has fixed an appropriate spatial relationship between the entities.

Using a lock that limits the position of the treatment catheter in one manner or another avoid the need for repeated user manipulation or stabilizing the position of devices. Either approach significantly simplifies a procedure in which repeated positioning of the access device is required to reach multiple treatment sites.

Another aspect of the invention that can simplify the requirements for user manipulation involves a shape memory wire, motor or electroactive polymer structure to actuate the treatment device active member. By using a shape memory alloy (SMA) wire or another similar means, electrical potential can be applied to the element to cause it to contract to actuate a basket, etc. Such action may be electronically controlled to automatically trigger upon advancement of the distal end of the treatment device beyond the access device. Alternatively, the electroactive element may be activated by a manual switch or semi-automatically activated by virtue of electrical contact made between electrodes positioned along the treatment and access device.

Several potential advantages are offered by using an electrically-driven means for, for example, basket deployment. As above, the feature may be employed to minimize operator steps. Yet, even where manual activation is required by a user, the electronic actuation means may offer certain advantages. Specifically, an SMA element can be designed to offer a great deal of actuation force. Such potential may be desirable in that it may employed to actuate stiffer basket members than otherwise practical for direct user manipulation.

A stiffer or more robust active end may be advantageous for reason of being less susceptible to inversion or other unwanted deformation of its members when interacting with anatomy to be treated. Such a device may have less need for a flexure or joint as described herein. Accordingly, this aspect of the invention offers another advantageous alternative for improving device efficacy.

Yet another aspect of the invention includes kits having any combination of devices described herein—whether provided in packaged combination or assembled by a technician for operating use, instructions for use, etc.

BRIEF DESCRIPTION OF THE DRAWINGS

Each of the following figures diagrammatically illustrates aspects of the invention. Variation of the invention from the aspects shown in the figures is contemplated.

FIG. 7 offers a side sectional view an airway where the junction comprises a tether-based variation of the invention.

FIG. 8A is a side sectional view of yet another variation of the invention in which the alignment of the active member and navigability of the device rely on a combination of the flexibility of the device with an addition support.

FIGS. 9A and 9B show side and end views of another active member.

FIG. 15A is a side section view of an improved construction approach for making a treatment device according to the present invention; FIG. 15B is an end view of component employed in the device shown in FIG. 15A.

FIGS. 16A-16C show side views of various stop or lock members as may be employed in connection with a treatment and/or access device according to another aspect of the invention.

DETAILED DESCRIPTION

It is understood that the examples below discuss uses in the airways of the lungs. However, unless specifically noted, the invention is not limited to use in the lung. Instead, the invention may have applicability in various parts of the body. Moreover, the invention may be used in minimally invasive procedure, or open surgical procedures where orientation and alignment features are desired.

Generally speaking, the invention includes medical devices including an elongate member with an active distal end, where a junction is provided between the two structures. The junction permits rotation or angular adjustment of the active end relative to the elongate member in order to better situate the active end for contacting the tissue wall of a cavity or passageway give misalignment between such structure and an access pathway. The invention includes methods of using such devices, where the device permits adjustment or realignment improved active member orientation or placement. Variations may include devices where adjustment occurs without specific user reorientation/manipulation of the device.

Figure 1:
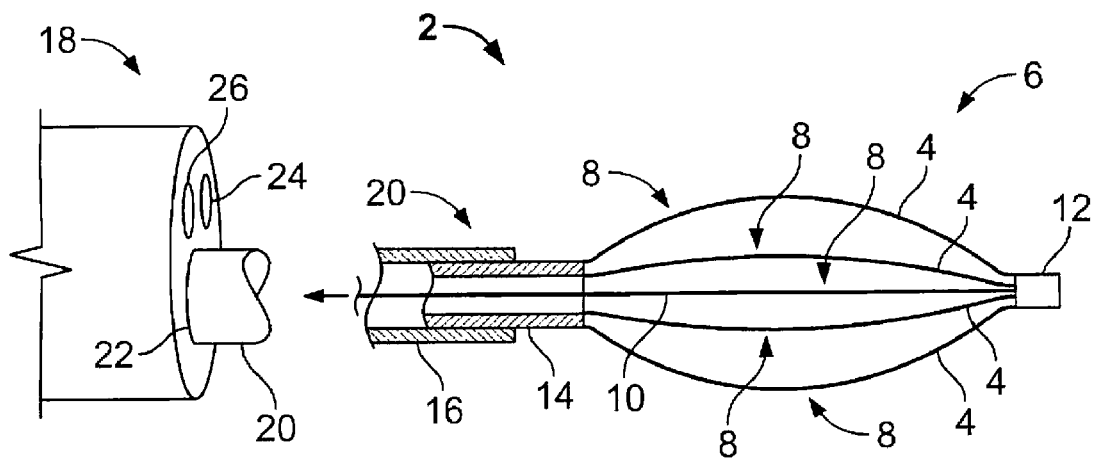
FIG. 1 is a side view of a customary medical device having an elongate member and an active distal end for treating tissue using energy delivery.

Turning now to the figures, FIG. 1 illustrates an example of an energy transfer device 2 having arms 4 configured in the form of a basket 6 that may expand to apply treatment to a body passageway, cavity, lumen, etc. No flexible joint or junction structure is shown in this device. Such a device is shown and described in U.S. patent application Ser. No. 09/436,455, entitled, "DEVICES FOR MODIFICATION OF AIRWAYS BY TRANSFER OF ENERGY," which is incorporated herein by reference in its entirety, especially for its disclosure of alternative active member and overall device configurations applicable to the present invention.

Specifically regarding the device shown in FIG. 1, however, basket shape may expand radially during use to a working diameter in effort to achieve contact between the arms carrying electrodes 8 and the airway walls. The arms may also include temperature sensors.

The wire 10 extends through a lumen of the elongate catheter body 14, to which the active member (in this case, basket 6) is directly mounted. The treatment device a may be delivered to a treatment site through a delivery sleeve or sheath 16. Note, however, that wire 10 may be omitted. In which case, the mechanism for expansion will be elastic, superelastic, or shape memory recovery of the electrodes from a compressed configuration from within sheath 16. In other words, basket 6 may expand upon activation by the user, or it may automatically expand when advanced out of a restraining sheath (or the sheath is withdrawn proximally from the basket). The wire 10 may be used to deliver energy to the active member and/or assist the active member in expanding.

Energy transfer device 2 is shown in association with a bronchoscope 18. The elongate shaft 20 of the device is received within the working lumen 22 of the bronchoscope. Note that the working lumen is offset from center. Such a configuration maximizes space available for an aspiration lumen 24 and an imaging lumen 26 that may contain a fiber optic cable or other visualization means.

Figure 2A:
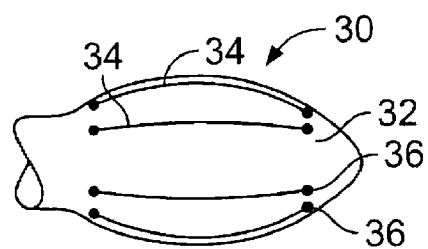
FIGS. 2A-2H illustrate alternate active end configurations as may be used in the present invention.

FIGS. 2A-2H show active members that may be used for treatment device 2 in lieu of basket 6 or in a treatment device according to the present FIG. 2A shows a variation of an active member 30 in the form of a body 32 having a set diameter and length. Electrodes 34 are shown secured to the body through holes 36. The electrodes are oriented axially. The diameter of active member 30 is set to correspond to that desired for treating a given body lumen or passageway.

In the case of a wire frame or basket, its members will generally be symmetrically deployed. This shape may be round, rounded or polygonal in cross section. Other configurations, including asymmetrical active member configurations are described below.

Figure 2B:
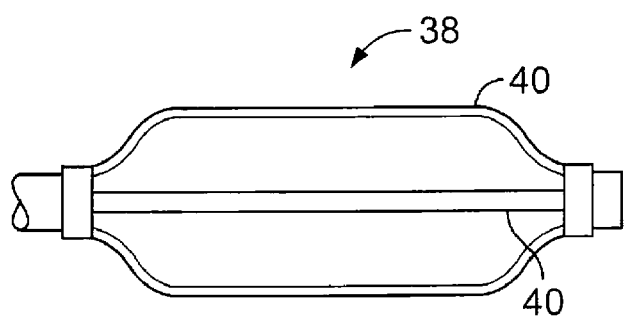
Figure 2C:
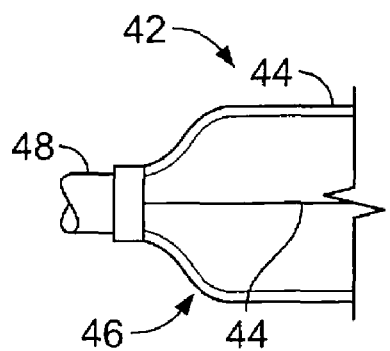

First, however, FIG. 2B shows an active member 38 in the form a balloon. The balloon may have electrodes, heating elements, or sensors 40 on its surface. The electrodes will move outward upon balloon inflation. Active member 40 in FIG. 2C comprises at least one arms 42. As with the basket, the arms may themselves be the electrodes, or they may carry them. Where at least two arms are provided, they may be symmetrically deployed. Whether one arm is provided alone or a plurality are to be used, an offset 46 may be provided so that the member(s) extend beyond the diameter of the elongate member or base 48 of the structure.

Figure 2D:
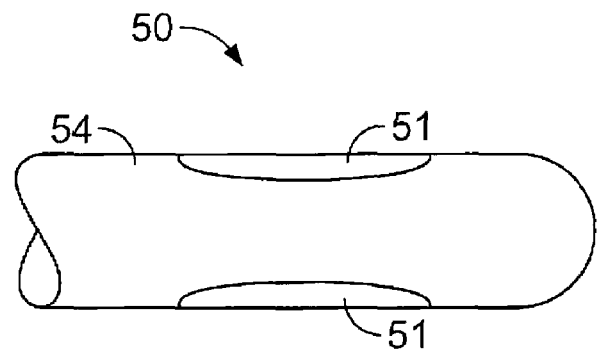

Active member 50 shown in FIG. 2D is another variation of the invention. This variation includes at least one energy transfer window 52 set in the active member body 54. The windows may be glass, plastic or another material substantially transparent to visible light, infrared radiation or ultraviolet radiation, etc. In use, a light, infrared or ultraviolet source such as a laser diode, fiber optic connection, etc. (not shown) would delivery energy to a tissue target site via the windows to effect treatment. Alternatively, the windows may be an electrode itself.

Figure 2E:
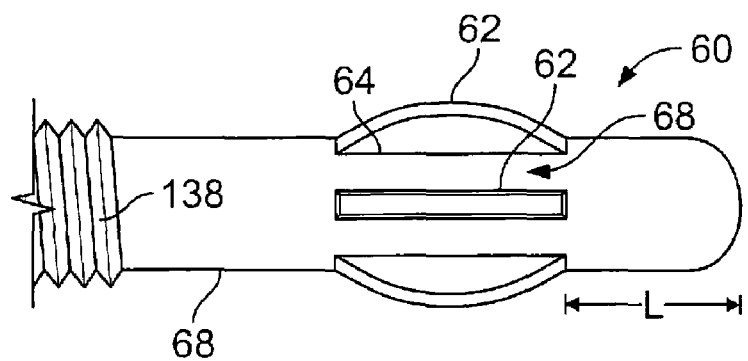

Active member 60 in FIG. 2E offers another configuration employing electrodes. In this variation, electrodes 62 are bowed outward from openings 66 in an elongate active member body 68. The electrodes need not extend from the body of the device. In any case, active member 60 is configured such that its end extends some distance beyond the electrode or other active elements for energy delivery. A length "L" of the extension section may be longer or shorter. In any case, the active member variation in FIG. 2E provides an example in which active element(s) of member 60 are located proximal of the distal tip of the elongate member. FIG. 2D illustrates this principle as well.

Figure 2F:
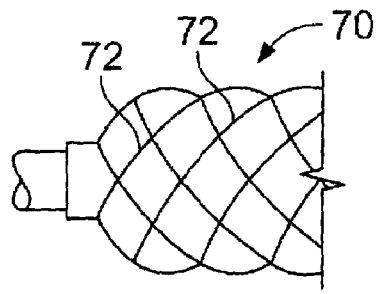
Figure 2G:
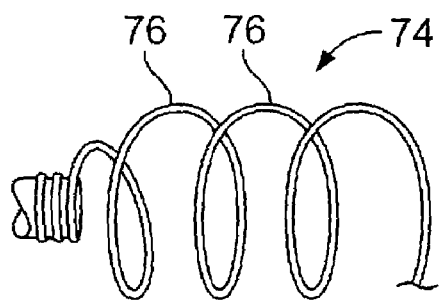

FIG. 2F shows an active member 70 in the form of a scaffolding, comprising a plurality of struts 72 (e.g., similar to a stent or frame structure). Active member 74 in FIG. 2G is another scaffolding type of device, in which the scaffolding is formed by a plurality of turns 76 of a coil. As for electrode placement, the bodies of the structures may serve as electrodes, or the structure may carry electrodes wired to the scaffolding structure.

Figure 2H:
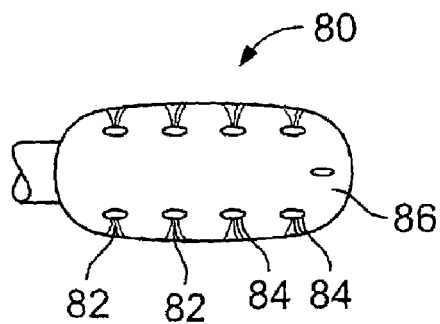

It is worth noting that each of the active members in FIGS. 1 and 2A-2G are adapted to transfer energy to a tissue structure (or possibly carry sensors for temperature detection, mapping, etc.). However, active member 80 in FIG. 2H is suited for transferring energy from tissue. Chilled fluid 82 can be delivered to adjacent or contacting tissue way of orifices 84 in shell 86. The active element could be another form of cooling element, such as a thermoelectric junction, or a material cooled by the expansion of compressed gas within the device. As such, the active members may collectively be regarded a devices adapted to transfer energy with (to or from) tissue. In addition, active member variation 80 in FIG. 2H could be used for delivering a compound to chemically alter or effect tissue at a treatment site.

Figure 3:
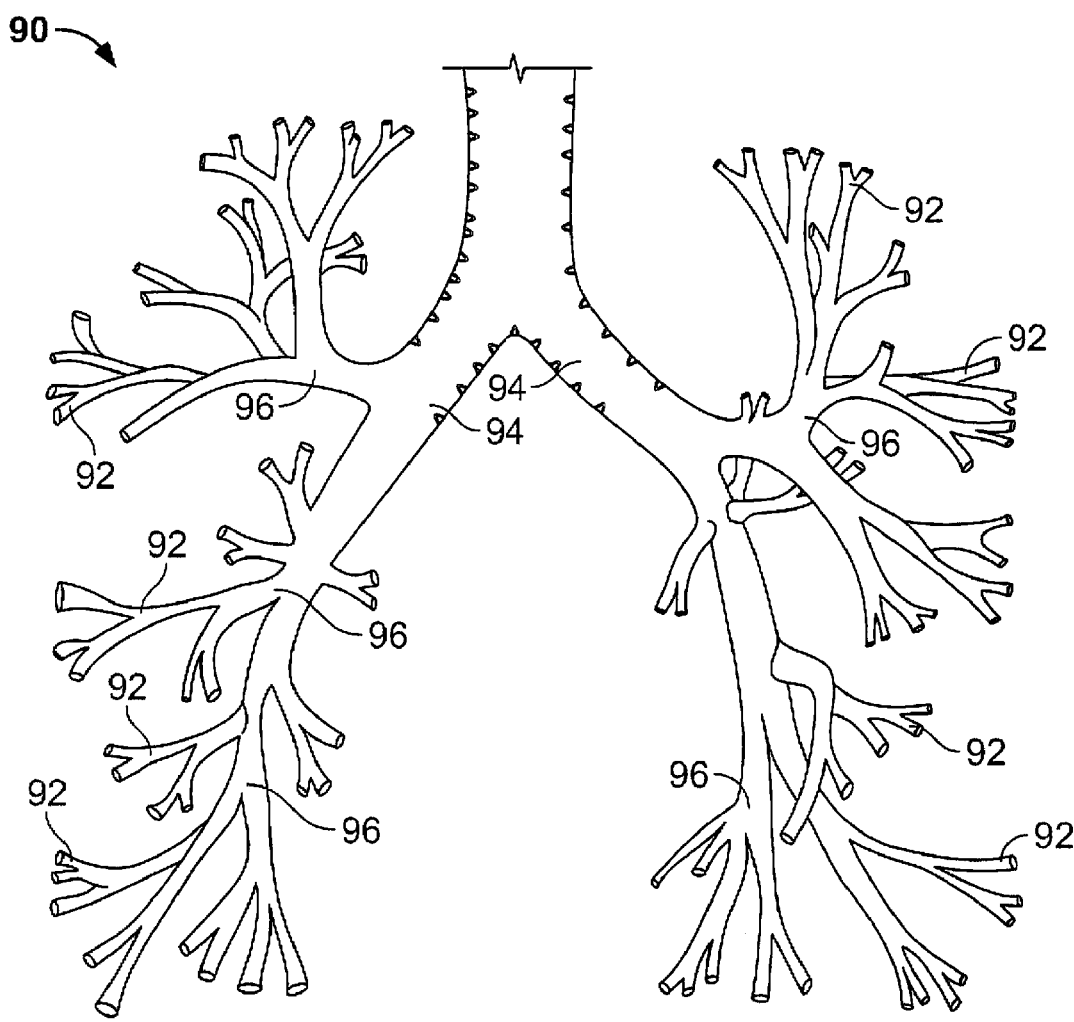
FIG. 3 is an illustration of the airways within a human lung.

FIG. 3 illustrates a bronchial tree 90. As noted herein, the devices of the present invention are suited for use in multiple locations within the body. However, the bronchial tree offers an example of one environment in which the subject devices or devices like those in FIG. 1 may be put to use. As shown, the various bronchioles 92 decrease in size and have many branches as they extend into the right and left bronchi 94.

Figure 4A:
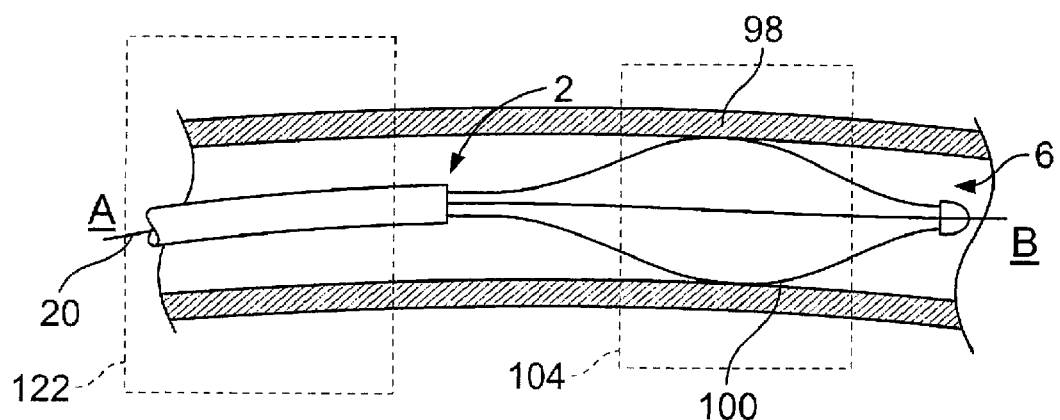
FIGS. 4A and 4B are side sectional views of bronchi illustrating use of the device of FIG. 1, where misalignment causes distortion of the device.
Figure 4B:
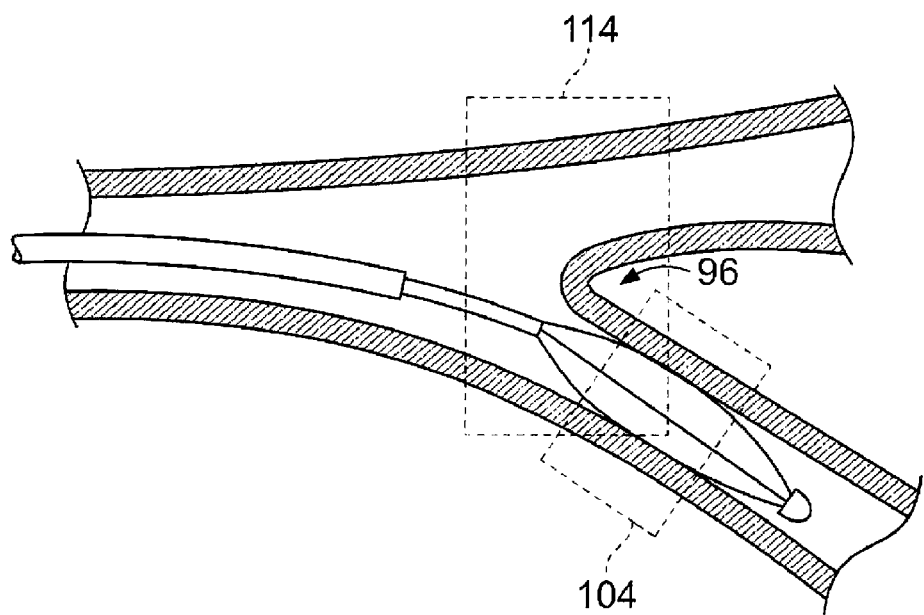

FIGS. 4A and 4B illustrate the potential for distortion of the device. In FIG. 4A, device 2 is seen within an airway or lumen 98 with basket 6 open. The device expands such that it makes the desired contact with points around an inner wall 100 of the airway. As illustrated, alignment of the access path 102 with the lumen 102 (and/or with the target area 104) increases the ease in which the operator achieves the desired contact with the tissue 100. As shown in FIG. 4A, when the access path 102 leading to the target area 104 (as designated by axis "A") permits alignment with the device or device shaft 20 (as designated by axis "B") there is lessened probability that the device unacceptably distorts or deflects from the target area 104. It should be noted that the access path may be considered natural or created pathways within the body. Alternatively, or in combination, the access path may include catheters, scope-type devices, or other such devices used to advance a treatment device.

In contrast, as shown in FIG. 4B, device 2 becomes substantially misaligned or distorted when treating a branching section 96 of the airway. In the illustrated case, it is difficult to define either one of an axis A or B because of the curvature imparted upon the device. Still, one can appreciate the misalignment of active member 6 and elongate member 20.

As shown, the device curves when passed into a branching airway. As a result of misalignment of these anatomical structures, the proximal portion or the shaft 20 of the device is misaligned within the treatment area 104. This misalignment causes the active end 6 to distort within airway 110. In the illustrated example, the upper and lower arms 4 of the basket are prone to undesired deformation (such as splay or inward deflection) as they react to forces caused by flexing of the device when trying to accommodate the turn. In some cases, deformation causes one or more of the arms 4 to "invert" which, if not corrected, increases the chance of undesired treatment.

Figure 5A:
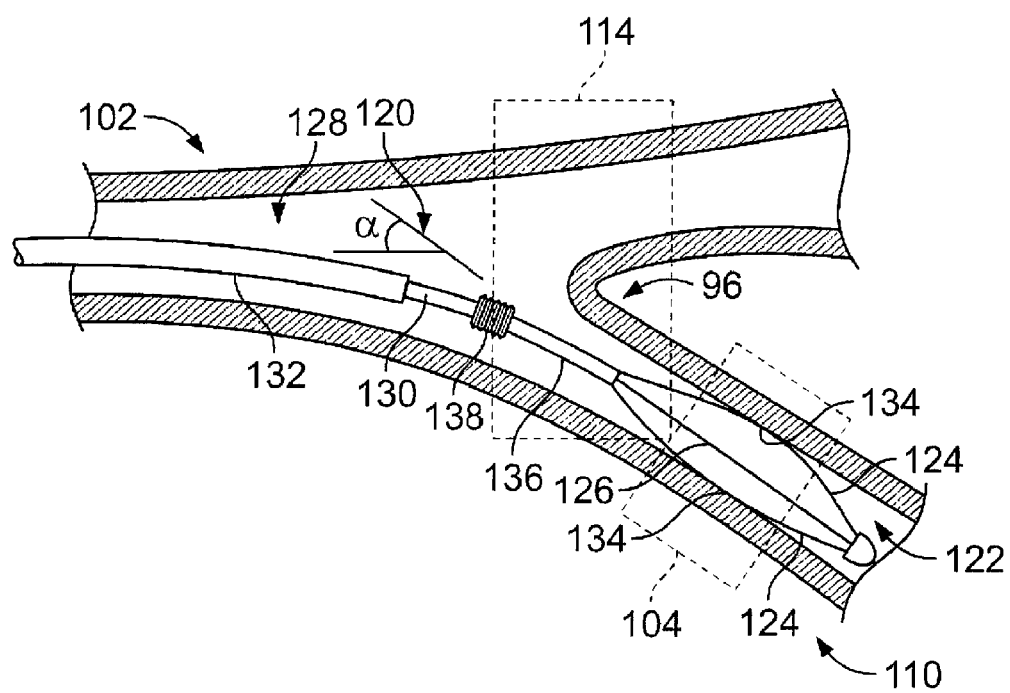
FIGS. 5A and 5B also provide side sectional views of a device of the present invention being advance in an airway.

In contrast, the electrodes of a device according to the present invention are less prone to distortion under identical conditions. FIG. 5A provides such an illustration in which the alignment of the device is closely matched to the alignment of the airway. It is noted that the present invention also benefits those cases in which the pathway and target site are offset as opposed to having an angular difference.

As with device 2, a variation of the inventive device 120 includes an active member 122 in the form of a basket made from a plurality of arms 124 and having a core wire 126 to open or adjust the basket size. The basket is connected to an elongate shaft 128. The shaft is shown comprising an inner member 130 and an optional sleeve 132. Electrical leads to electrodes 134 or electrode portions of arms 124 are houses within inner member 130.

The distal end of the device comprises an active member such as a basket 112, a member as shown in any of FIGS. 2A-2H or another appropriate structure. An extension section 136 of the active member 122 may be provided. Whether an extension is provided or not, the active member is connected to the elongate shaft member by a junction 138.

The junction functions to eliminate the need for the axis of the active portion to be aligned with the remainder of the device in order to provide substantially even tissue contact. The junction may be a joint, a flexure or equivalent means. A non-exhaustive listing of examples is provided below.

As for the action the junction enables, it allows the distal end of the device to self-align with the cavity or passageway to be treated, irrespective of the alignment of the access passageway. FIG. 5A illustrates an example of where the access passageway and passageway to be treated are misaligned by an angle α of about 20 degrees. In the example shown in FIG. 5B, the misalignment angle α is about 45 degrees. Yet, active end 122 of treatment device 120 is substantially aligned with the treatment area 104 in the subject airway 110.

At the same time, flexure or hinging action located primarily at the junction allows shaft 128 to remain substantially aligned with the access path 102 along lumen 110. Configuring the device with a junction that permits the constituent parts of the medical device (at least the active end 122, anyway) to align with cavity or passageway to be treated avoids unwanted deformation and flexure of the active member or its constituent elements. With its shape substantially maintained (or in the case of a rigid body where shape will not change to accommodate opposing anatomy at all) and good alignment with the subject tissue to be treated, consistent device performance in energy transfer or other applications can be expected.

As mentioned above, the wall of the cavity or passageway to be treated may be located in the lung, or various other body organs or anatomical structures. Indeed the access path to the specific treatment site (i.e., the wall or tissue surface) may include part of the lumen/passageway or cavity itself. The invention finds use in any such situation where the region to be treated is misaligned with the access pathway. It is for this reason that devices according to the present invention may advantageously be used not only in treating branching anatomies such as in the lungs, but also turning or tortuous structures such as sections of the colon or stomach, especially when accessed through the esophagus. Indeed, the devices are advantageously used in any situation where the access path to a treatment site is misaligned with the working end of the device.

Figure 5B:
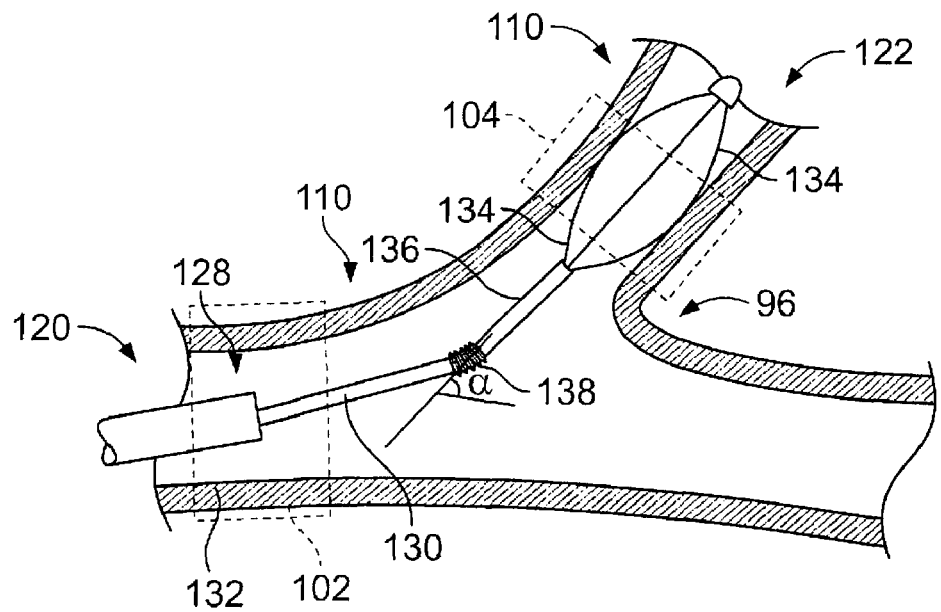
Figure 5C:
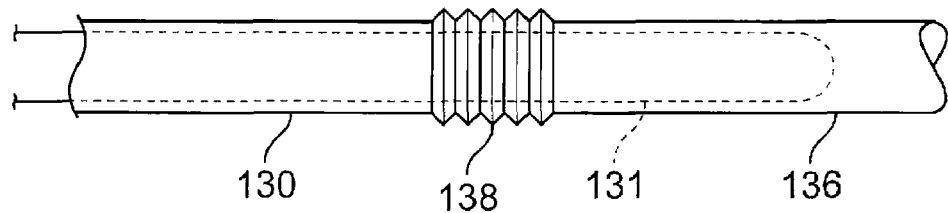
FIGS. 5C and 5D illustrate a variation of the invention with a reinforcing member.
Figure 5D:
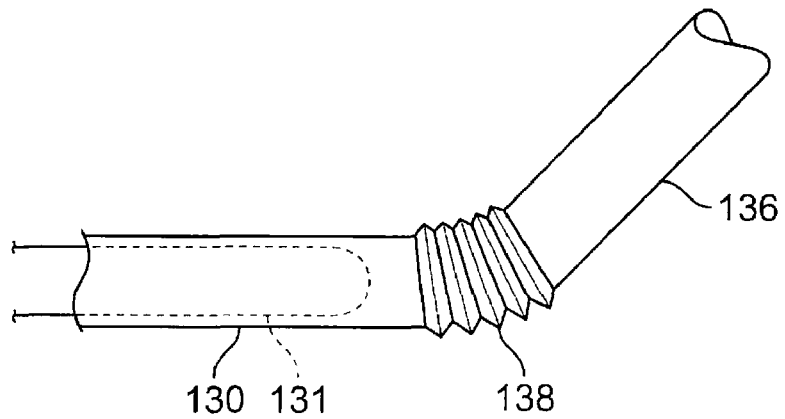

FIGS. 5C and 5D illustrate an additional variation of the invention disclosed herein. In this variation the junction 138 may be reinforced with a reinforcing member 131. As shown in FIG. 5C, the reinforcing member 131 maintains the device or shaft 130 or 136 in an aligned position, preferably for insertion, removal, and or navigation of the device. When desired, the reinforcing member 131 may be removed from the junction 138 as illustrated in FIG. 5D. Accordingly, upon removal, the device is free to flex or orientate as desired. Furthermore, the reinforcing member may be reinserted within the junction 138 when repositioning or removing the device from the target site. In additional variations, it is contemplated that the reinforcing member may be placed external to the device/junction.

Figure 6A:
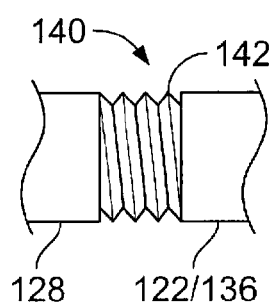
FIGS. 6A-6J illustrate examples of various proximal/distal end junctions for use in the subject invention.
Figure 6B:
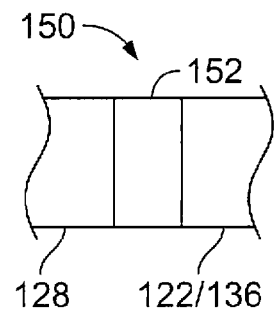

Whatever the application, FIGS. 6A-6I illustrate junctions for use in a device according to the present invention. As for these examples, FIG. 6A illustrates a junction 140 in the form of a plurality of turns or coils 142 of a spring. One side of the spring is connected elongate member 128 and the other directly to the active member 122 directly, or via an extension piece 136. The coil offers a flexure with 3-dimensional freedom allowing realignment of the active end of the subject device in any direction. Of course, a simple hinge may also be employed.

The length of the junction (whether a spring junction 140 or some other structure) may vary. Its length may depend on the overall system diameter. It may also depend on the degree of compliance desired. For example, with more turns of the coil, the junction becomes less rigid or more "floppy".

In any case, it may be desired that the junction has substantially the same diameter of the device structure adjacent the junction. In this way, a more atraumatic system can be provided. In this respect, it may also be desired to encapsulate the junction with a sleeve or covering if they include open or openable structure. Junction 138 shown in FIGS. 5A and 5B is so-covered. A covering can help avoid contaminating the joint with body fluid or debris which could compromise junction function.

Some of the junctions are inherently protected. Junction 150 shown in FIG. 6B comprises a polymer plug 152 or a section of polymer having a different flexibility or durometer than adjacent sections. When a separate piece of polymer is to be employed, it can be chemically or heat welded to adjacent structure; when the junction is formed integrally, this may be accomplished by selective vulcanizing, or reinforcement (even with a braid or by other means of forming a composite structure). Generally, it is noted that any connection of pieces or construction provided may be produced by methods known by those with skill in the art.

Figure 6C:
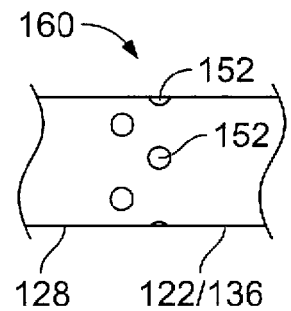
Figure 6D:
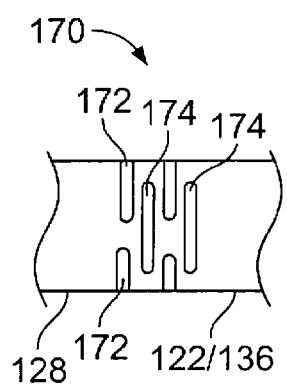

As for junction 160 shown in FIG. 6C, it is formed by removing sections of material from the body of the device. Openings 162 formed at the junction may be left empty, covered or filled with a more compliant material. FIG. 6D also shows a junction 170 in which openings are provided to provide increased flexibility. Here, openings 172 and 174 are offset from each other to form a sort of flexible universal joint. In either junction variation shown in FIG. 6C or 6D, the size, number shape, etc. of the opening may vary or be tuned as desired.

Figure 6E:
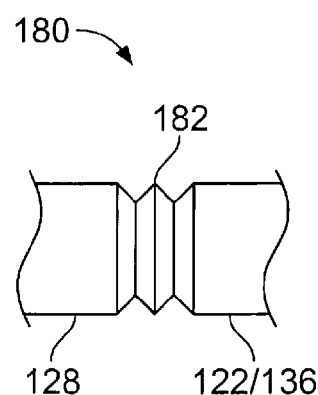

FIG. 6E shows a junction 180 in the form of a bellows comprising plurality of pleats 182. Here too, the number of pleats, etc. may be varied to achieve desirable performance.

Figure 6F:
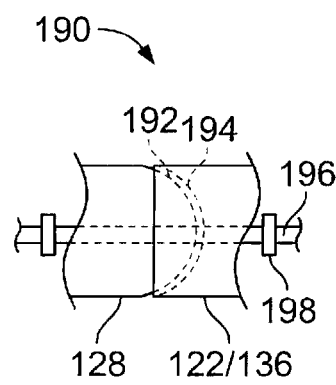

Junction 194 in FIG. 6F shows a true "joint" configuration. In this case, it is a universal joint provided by ball 192 and socket 194. These element may be held together by a tie wire 196, possibly with caps 198. Other configurations are possible as well.

Figure 6G:
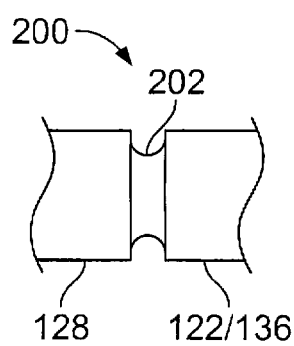
Figure 6H:
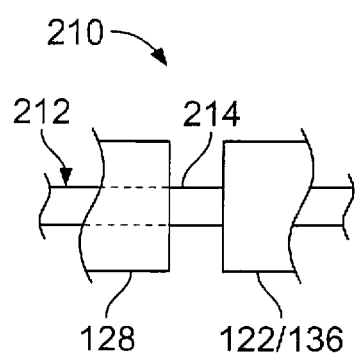

FIG. 6G illustrates a junction 200 in the form of a reduced diameter section 202. This variation offers greater flexibility by virtue of its decreased moment of inertia at the junction. While section 202 is integrally formed, the related junction 210 in FIG. 6G is formed from a hypotube or wire 212 having an exposed junction section 214 between elements 128 and 122/136. Variations of the invention will permit a junction having a reduced bending moment of inertia section as compared to the remainder of the device and/or shaft of the device. Reducing the bending moment of inertia may be accomplished in any number of ways. For example, there could be an area of reduced diameter, a section of material having a lower modulus, a section having a different shape, a flexible joint structure, etc. It should be noted that there are many additional ways to reduce the bending moment that will be readily apparent to those skilled in the art viewing the invention disclosed herein.

Figure 6I:
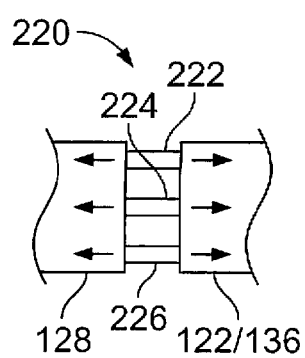

Yet another junction example is provided in FIG. 6I. Here junction 220 comprises a plurality of wires 222, 224, 226. In one variation, the wires simply offer increased flexibility of the junction. In another variation, the wires serve as an "active" or "dynamic" junction. The wires may be adjusted relative to one another to physically steer the distal end of the device. This junction may be manipulated manually with an appropriate user interface—especially one, like a joy-stick, that allows for full 3-dimensional or rotational freedom—or it may be controlled by automation using appropriate hardware and software controls. Of course, other "dynamic" junctions are possible as well.

Figure 6J:
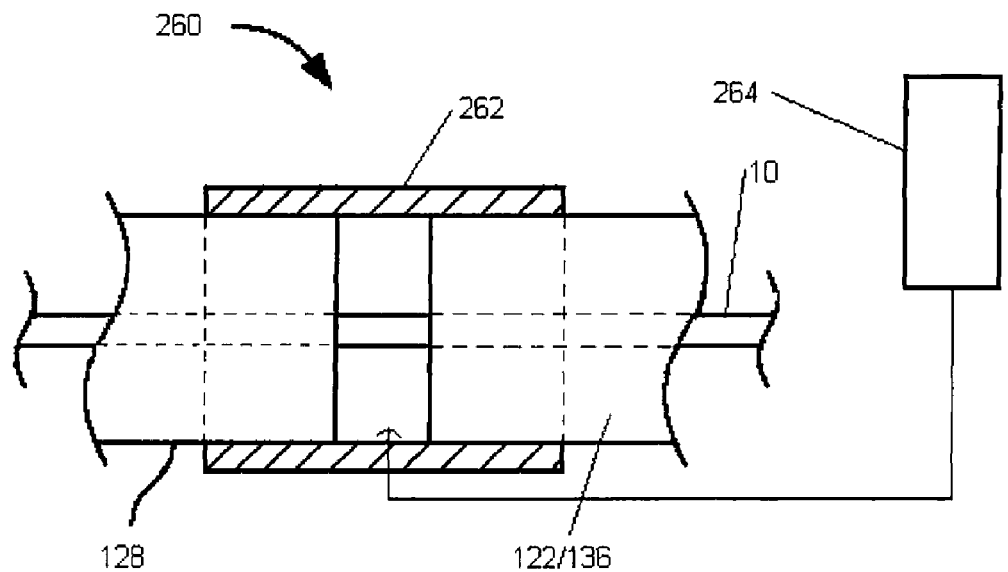

FIG. 6J shows another joint configuration 260 employing an external sleeve 262 between elongate member 128 and active member 122 directly, or extension section 136. A moveable wire 10 to actuate a distal basket or the like is also shown. The space between the wire and sleeve may be left open as shown, or filled in with a flexible polymer 264, such as low durometer urethane, a visco-elastic material, etc. Though not necessary, providing an internal member may improve system pushability. The sleeve itself will typically be a polymeric sleeve. It may be heat-shrink material such as PVC tubing; it may be integrally formed with either catheter body portion and press fit or slip fit and glued over other etc.

Because it is to the outside of the catheter body, it will typically be thin-walled and/or made of highly flexible material so the overall junction is sufficiently flexible. The sleeve could comprise a metallic braid. However, heat-shrink tubing offers particular advantages in terms of assembly or construction. In instances where the treatment device body 128 is made of a material such as PET that is susceptible to distortion by heating during shrinking of the sleeve, the body may be covered by a hypotube or another masking structure to protect it from undesirable heating.

Figure 6K:
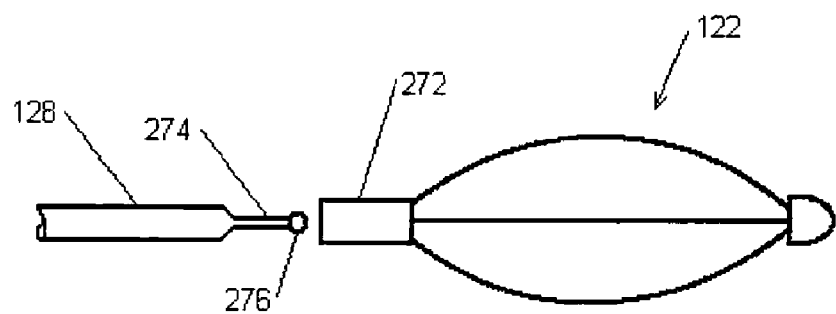
FIGS. 6K and 6L show another end junction approach with its components, and illustrating their manner of assembly, respectively.
Figure 6L:
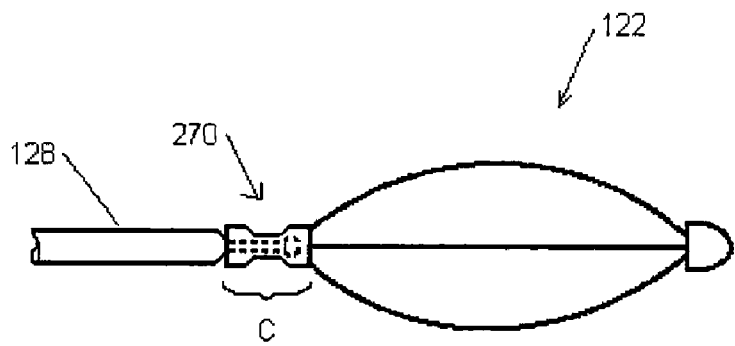

FIGS. 6K and 6L show another type of junction 270. It too offers relative ease of construction. In FIG. 6K, the constituent parts are shown alone. These include an active end 122 connected to a hypotube 272 section. Elongate member 128 tapers to an extension section 274 tipped with a welded ball end or solder ball 276. As shown in FIG. 6L, the members are assembled and connected to one another by crimping the tubular member over the extension 2274 at location "C".

The crimped section is collapsed to such a degree that it retains ball 276, but collapsed into contact with the extension. So-constructed, the active end is able to pivot about the ball section—serving as a "loose" joint. In addition, the tapered extension offers increased flexibility in the region, helping define a flexible junction portion.

Though not required, many variations of the invention allow for pushing the device from its proximal end to navigate the distal end through various sections of anatomy. To do so, the junction may be configured so that it does not or does not substantially decrease in the column strength of the overall device. The junctions shown in FIGS. 6A-6L may offer such column strength.

In contrast, the junctions incorporated into the devices in FIGS. 7 and 8A-8C are "floppy" (i.e., without sufficient column strength for the device to be pushable for navigation). In FIG. 7, a tether 230 connects active member 122 to inner member 130 of elongate member 128. The tether may simply comprise a flexible wire or cable, it may comprise a plurality of links, etc. The tether variation of the invention also accommodates relative motion between the device and the body (e.g., tidal motion of breathing, other muscle contractions, etc.) The tether permits the device to move relative to its intended treatment location unless the user desires and uses the tether or the sheath to pull the device back or drive it forward.

To navigate such a device to a treatment site, sleeve 132 is set in an arrangement adjacent to or covering at least a portion of active member. In this manner, the column strength provided by the sleeve allows for advancement of the active member within the subject anatomy.

The same action is required to navigate the device shown in FIG. 8A. What differs in this variation of the invention, however, is that the "tether" is actually a continuation of a highly flexible inner member 232. In this case, sleeve 234 of the shaft is shown with a thick or reinforced wall. In such a device, the sleeve carries the compressive loads on the device back to its distal end.

In other variations of the invention, the inner member that may do so. For example, in variations of the invention where no sleeve is provided (e.g., those that have an active end that does not change in diameter), then one elongate member may bear the load alone. Another example of a device in which the inner member carries the compressive loads is shown if FIGS. 8B and 8C.

Figure 8B:
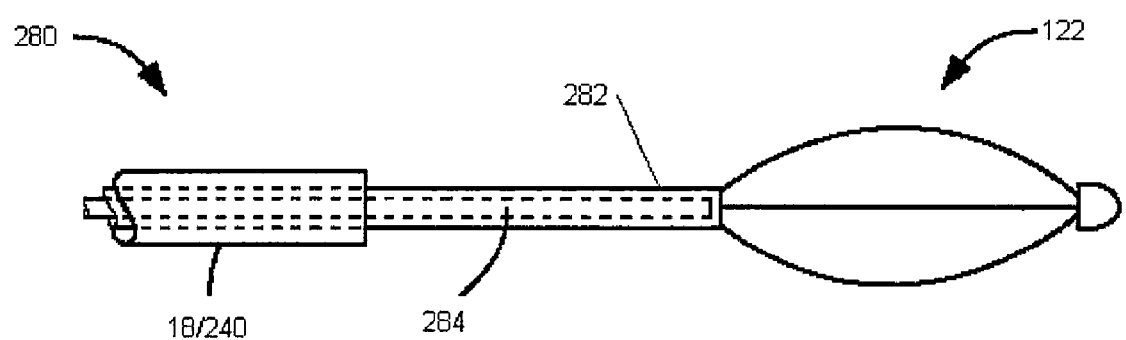
FIGS. 8B and 8C show a related variation in which an internal reinforcing member provides support to alternatively straighten and allow the device flexibility.
Figure 8C:
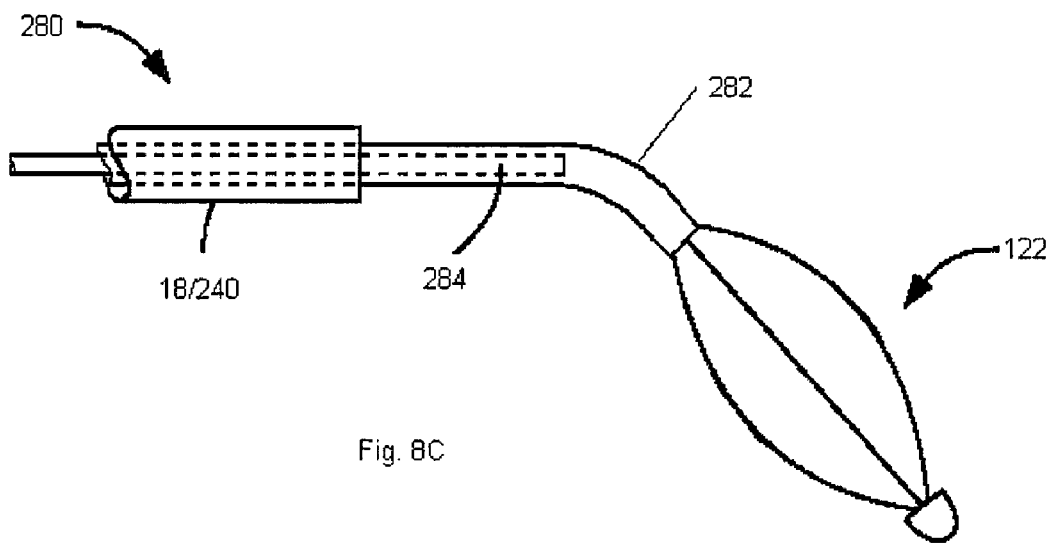

Like the device in FIG. 8A, device 280 in FIGS. 8B and 8C have a highly flexible elongate body 282. However, instead of a stiffening external sleeve, device 280 employs a stiffening obturator or shaft 284 within a lumen of body 282. As shown in FIG. 8B, when the shaft 284 fills the lumen, the device is relatively straight or stiff. When the shaft is withdrawn as shown in FIG. 8C, the distal end of the device is "floppy" or easily conformable to the subject anatomy. With the shaft advanced substantially to the end of the device, it offers ease of navigation; when withdrawn, it offers a compliant section according to an aspect of the present invention.

In another variation of the invention, the junction is of the type shown in FIGS. 6A-6I, but the active member is of a different configuration. Specifically, FIGS. 9A and 9B show side and end views of another active member 122 adjacent a junction 138.

In this case, however, electrodes 234 are provided upon a face 236 of the device. An aspiration, irrigation, or insufflation lumen 238 may be provided amongst the electrodes or the device may be otherwise configured.

Figure 10:
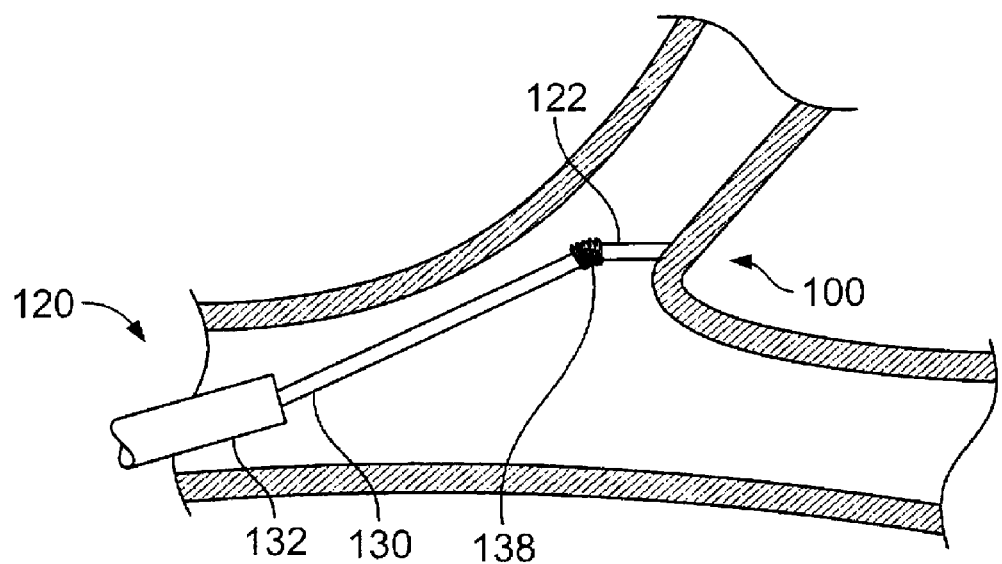
FIG. 10 is a side sectional view of bronchi illustrating use of a device according to the present invention that incorporates the active member shown in FIGS. 9A and 9B.
Figure 11:
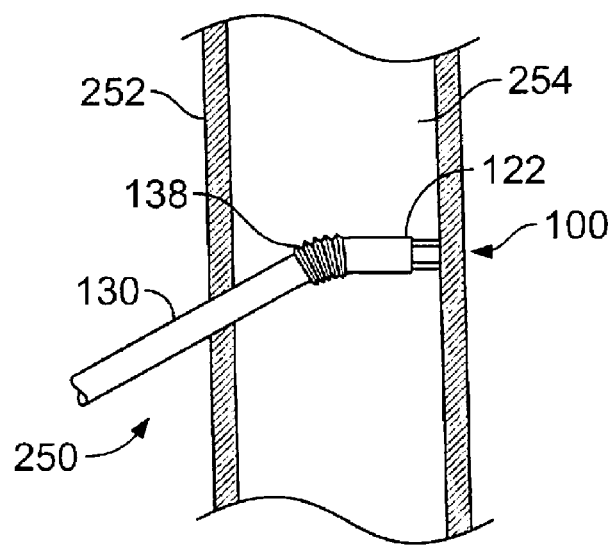
FIG. 11 is a side sectional view of an access layer and a tissue wall to be treated with a device including an active member as shown in FIGS. 9A and 9B.

Whatever form the active member takes, its approach to a treatment site will be end-on. In other words, the face of the device will generally be advanced to and be set in contact with or adjacent to a tissue wall 100. In the example shown in FIG. 10, the tissue wall is located within the branching airways of a lung. In FIG. 11, the tissue wall may be that of another organ. Specifically, it may be the external wall of an organ such as the heart, stomach, etc. In the latter case the access path will be thought an incision 250 in the skin 252 and abdominal tissue 252. The access path may be through the internal wall of an organ such as the heart, stomach, etc. In any case, FIG. 11 is intended to illustrate an example of basic percutaneous access to a treatment site.

In another approach to the invention, no junction, tether or floppy inner member need be provided. Advantageously, one may be employed, though it is not necessary. This aspect of the invention concerns a reconfigured bronchoscope 240 or another access device as referenced above that typically includes an offset working lumen.

Figure 12A:
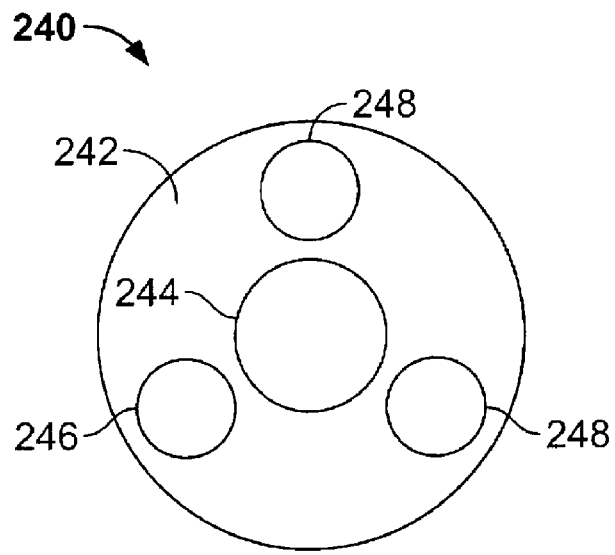
FIG. 12A is an end view of an endoscope employed according to one aspect of the invention.
Figure 12B:
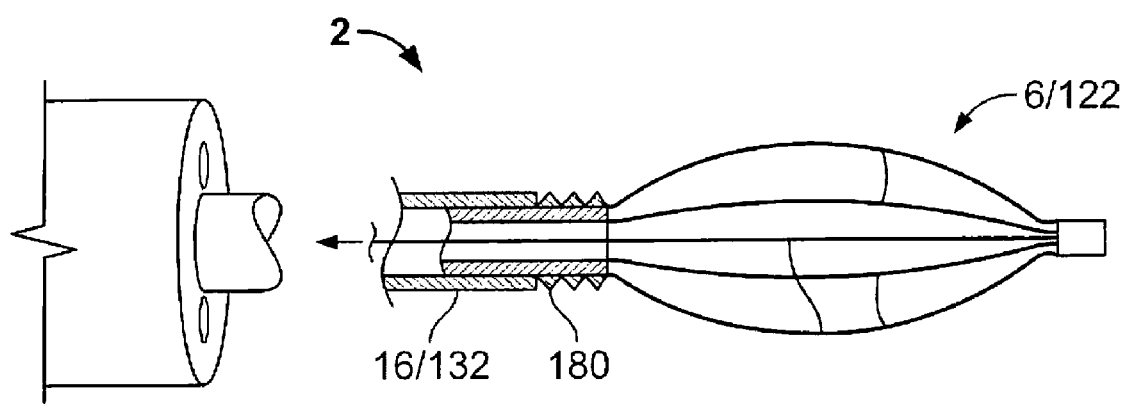
FIG. 12B is a side view of the bronchoscope of FIG. 12A with a treatment device received within its centered working lumen.

FIG. 12A illustrates the end 242 of such a device 240. Here working lumen 244 is centrally located. It may be at the exact center or be offset some small amount. An imaging lumen 246 for a vision system and/or a plurality of aspiration or vacuum lumen 248 may be provided in the device. As shown in FIG. 12B, when a device 2 or 120 is received within the working lumen of a bronchoscope having a working lumen set substantially at the center of the device, then, upon deployment the treatment device 2/120 is not already biased to one side as shown in FIG. 1. While such an offset or bias may offer an advantage in some circumstances, it exacerbates alignment problems in the opposite direction. Accordingly, use of a device as shown in FIGS. 12A and 12B, (especially in treating the bronchi) offers advantages in terms of consistency of approach without manipulation of the access device/bronchoscope.

Figure 13A:
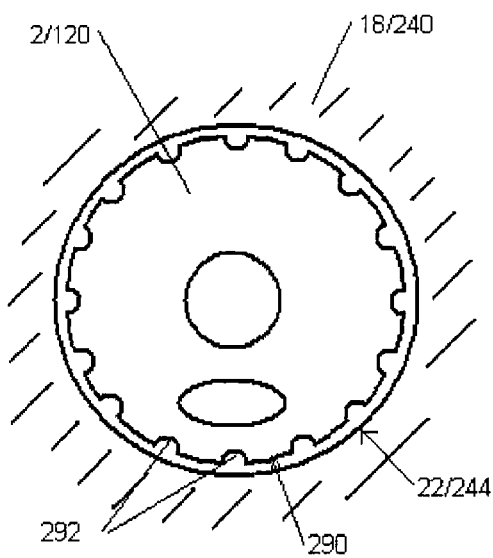
FIGS. 13A and 13B are end section views of first and second treatment systems with actuation improving features.
Figure 13B:
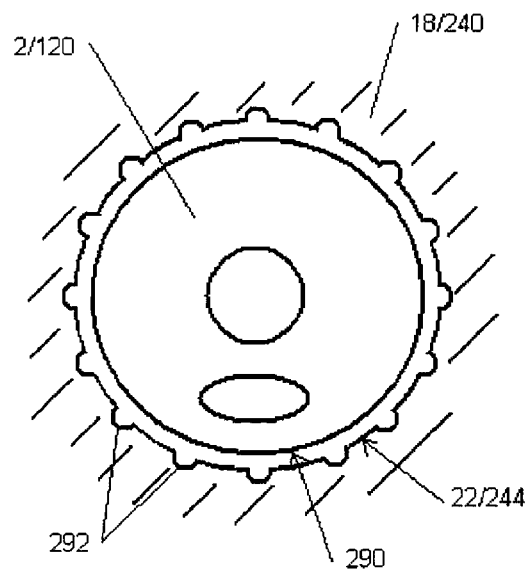

FIGS. 13A and 13B illustrate another means of improving the interaction between the treatment device 2/120 and its respective access device 18/240. In one manner or another, either one of the working lumen 22/244 of the access device or outer surface of the treatment device 2/120 is modified from a smooth to a textured, scalloped, ribbed, undercut, etc. geometry that results in a reduced area of surface contact between the members.

In addition, depending of the nature of the surface treatment, both of the working lumen and outer surface of the elongate member could receive surface modification. However, care should be taken such that any complimentary or interlocking/grabbing combinations are provided.

Regardless, the nature of the surface treatment may be consistent along the length of the respective members or it may vary. The interrupted surface shapes shown in FIGS. 13A and 13B may be easily extruded. Different shapes and configurations may be otherwise constructed. Still further, while the structures shown integrally include features to break-up a smooth surface (i.e., channels 2292), similar forms may be built-up using laminated constructions, etc.

Figure 14A:
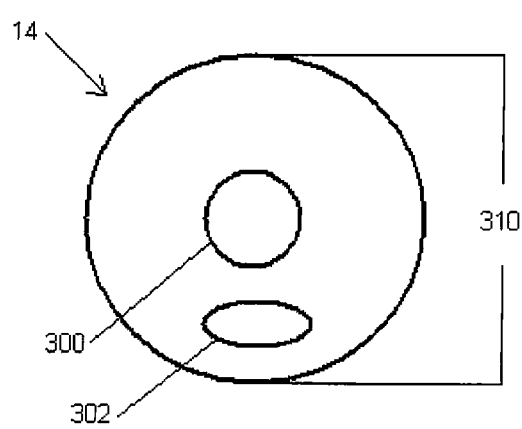
FIGS. 14A and 14B are end section views of a known treatment device body and one according to the present invention adapted for improved flex characteristics with maintained column strength, respectively.
Figure 14B:
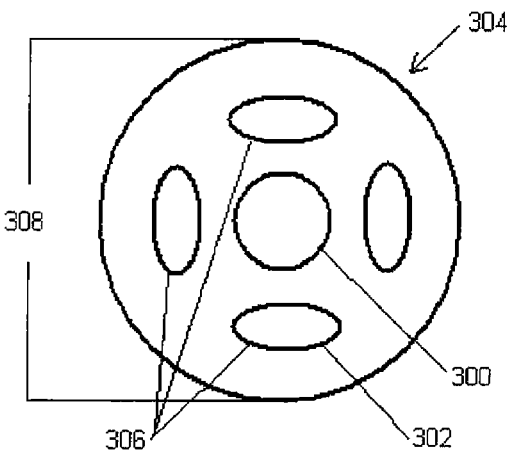

FIGS. 14A and 14B illustrate another means of improving overall system performance. FIG. 14A shows a cross-section of an inner member 14 of a known treatment device 2 such in FIG. 1. It includes a first lumen 300 for wire 10 to actuate a basket-type active end 6 and an offset thermocouple wire lumen 302. A body configured in this manner would obviously not offer consistent flexibility performance in every direction out of the cross section plane.

The cross-section of body 304 shown in FIG. 14B will offer much more consistent flexibility performance. The body also includes a pull wire lumen 300 and thermocouple lumen 302. In addition, it includes flex-balancing holes/lumen 306 symmetrically arranged around the remainder of the catheter body wall. Often, the openings themselves will be symmetrical.

In FIG. 14B, the configuration displays 4-way symmetry in that each quarter section of the cross-section matches the other. Greater or fewer degrees of symmetry may be employed. In one example, the structure may be balanced by three symmetrically spaced openings 302/304. In which case, the holes may be slightly curved or crescent-shaped rather than ovaloid to better wrap around the inner lumen. Alternatively, upwards of 5 or 10 simple circular holes may be employed. Many options exist within the spirit of this aspect of the invention.

Regardless of how flex is tuned, it may be desirable to maintain the column strength of the treatment device. This goal can be accomplished by increasing the outer diameter 308 of device cross-section 304 in comparison to the outer diameter 310 of device 14 cross-section as shown in FIGS. 14A and 14B. As stated above, maintaining or at least substantially maintaining the column strength of the device by adding material when other material is taken away is important in providing a device with sufficient pushability characteristics.

FIGS. 15A and 15B illustrate another potential set of improvements to ensure consistent performance of the subject devices. FIG. 15A provides a sectional view of a construction approach utilizing one or more collars 320 detailed in FIG. 15B. Each collar comprises a perforated disc, where holes 322, 324 in the body are adapted to receive arms 4 to form a basket 6, and a wire 10 to actuate the basket. Collar 320 may also include one or more additional holes 326 to pass thermocouple wire(s).

The collars provide a means of precision alignment, orientation, and for precisely generating even arm/leg 4 lengths for the basket 6. Such characteristics may result in more even actuation of the basket formed by the pieces.

An aspect of this variation of the invention involves the manner in which wire or ribbon segments 4 are attached to the collar(s) 320. Specifically, when welded, the location for the weld joint(s) are the exterior of the collar (as indicated at the points "W"). This way, sections of the arms/legs of the basket that are highly stressed in bending where they exit the collar(s) do not loose strength by annealing from the heat of welding. Otherwise, annealing can lead to members prone to plastic deformation and/or fatigue failure.

Other attachment approaches may be employed as well. Depending on the material selected for the collars, various attachment techniques ranging from co-molding the collars (if plastic) with arms 4, to bonding with adhesive, brazing, etc. may be employed. The welding technique discussed above is particularly useful when the collars and arms are made of stainless steel or other material that is easily welded together.

In any case, FIG. 15A illustrates other aspects of a preferred mode of constructing the subject treatment device 120. The figure illustrates a sleeve-type junction of the style shown in FIG. 6J connecting the treatment device elongate member 128 and an extension section 136. A wire 10 runs through each member and is shown secured by a ball end (in the for of solder, a weld bead or adhered member) at distal collar 328. Only two arms/legs 4 are shown for the sake of clarity in the drawing. However, more (e.g., four) may be employed in the basket 6 as shown elsewhere.

When a proximal collar 320 is provided, the arms/legs may be attached thereto by the techniques described above. To assist in positioning this collar relative to the extension shaft 136 or elongate member 128 (where no junction 260 and/or extension 136 is provided), the collar may include a recess 330 to center the members relative to one another.

When no proximal collar is used, extension member 136 may, alone, serve to stabilize and/or anchor arm/legs 4 at a proximal side. Indeed, FIG. 15A shows members 4 received through lumen 332 within the extension member body. The arms/legs may be held in place by thermoforming the extension to collapse upon the members. Alternatively, adhesive may be used within the lumen. Still further, the proximal ends of the arms/legs may be bent inward or outward to prohibit their withdrawal. To restraint arm/leg 4 movement in a proximal direction, the space between members 128 and 136 may include a plug 264 of flexible material therein. Of course, other joint or junction configurations could be used to the same effect.

FIGS. 16A-16C illustrate a number of locking mechanisms 340, 342, 344 as may be used in accordance with another aspect of the present invention. These locks or others may be used one either one of the treatment device 2/120 or access device 18/240. The lock or clip shown in FIG. 16A is a spring-clip type of device in which elastic bands 346 bias arms 348 in a collapsed configuration, with lever arms 350 provided to open the structure. The device shown in FIG. 16B is a cam-type lock in which lever arm 352 causes cam section 354 to pivot within body 356. The lock in FIG. 16C is a simple strew-type clamp where body 358 is compressed by turning screw knob 360.

These devices—or others like them—can be releasable secured to the treatment device/catheter to prove an adjustable depth stop for advancement of the treatment device within the access device. Whether fixed in position or adjustable, such a feature allows for ready repositioning of the treatment device to a desired insertion point within, for example, the bronchoscope working lumen for repeated insertion and withdrawal. It will also help to reliably achieve ideal position (as determined by the user or predetermined, given the system parameters) from the active end of the treatment device to the distal end of the access device.

Alternatively, structures 340, 342, 344 or ones like them may be incorporated in an access device. In which case, the incorporated device will simply lock the treatment and access device together in a desirable relationship. In this way, when the access device is moved the treatment device will follow with it. As such, user manipulation of the position of the access device will not give raise to a need to also adjust or actively maintain the relative position of the treatment device.

The locking mechanism shown and other releasable positioning devices (of a mechanical, pneumatic, etc. nature) are advantageous from the perspective of allowing for adjustable positioning of the access and treatment devices with respect to one another. However, fixed-position stops may be advantageous as well. For instance, the treatment device may include a leur fitting to lock that structure to the access device at a set location.

Alternatively, as illustrated in connection with FIG. 16C, a clamping device could include a leur fitting 362 so that once it is set in position upon the treatment catheter body, that the fitting is locked with a complimentary fitting piece 364 on the access device 18/240 to fix their relative position, rather than simply bottoming-out a stop surface 366 against the access device.

Any of these approaches offers an aid to the bronchoscopist or another operator of a different access device. They simplify the procedure, requiring less active control from the user.

Yet another aspect of the invention is directed toward simplifying the use of a device according to FIG. 1, or more preferably as shown in FIGS. 15A and 15B. Specifically, any such device can be configured so that wire 10 is an SMA wire. The wire itself may be NiTi alloy. Alternatively, the wire to actuate the basket 6 may be connected to an SMA coil or another structure such as an electroactive polymer actuator. In instances where the wire itself is an SMA element, it form part of a circuit with a return wire lead (not show) so that current passing through the wire will cause it to heat and then contract. "Muscle wires" operating on this principle are well known.

The spring action of the basket and/or urging the basket into to a linear configuration upon withdrawal into a sleeve 16 or bronchoscope working lumen 22/244 (after cutting power to the wire) will stretch the wire, readying the structure for another deployment cycle. Alternatively, a 2-way shape memory alloy may be employed.

By using an SMA element or another means, electrical potential can be applied to the element to cause it to contract to actuate the basket or another active member. Such an approach offers efficiency gains in carrying out a procedure since no user action is required to physically actuate a cable, lever, etc. to expand the active end of the treatment device. In addition, the basket actuation means employed may offer greater actuation force than an operator can easily apply.

With this additional force or work potential, it is feasible to configure a treatment device with a more robust active end. By using stiffer members (e.g., made of thicker or stronger material, employing a laminate construction, etc.) a system can be provided that is less prone to undesirable deformation because of contact with tissue. With a sufficiently rigid active distal member, the tissue being treated in some cases can be forced to conform to the device rather than vice versa as with the variations of the invention employing a junction described above. Still, each inventive variation offers its own benefits and will excel in use under different conditions.

As for other details of the present invention, materials and manufacturing techniques may be employed as within the level of those with skill in the relevant art. The same may hold true with respect to method-based aspects of the invention in terms of additional acts a commonly or logically employed. In addition, though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. Also, it is contemplated that any optional feature of the inventive variations described may be set forth and claimed independently, or in combination with any one or more of the features described herein. Reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

CLAIMS

The breadth of the present invention is not to be limited by the subject specification, but rather only by the plain meaning of the claim terms employed. That being said,

We claim:

1. A medical device for treating tissue within a lung, comprising:
   an elongate shaft;
   an elongate member slidably located external to the elongate shaft such that the elongate shaft and elongate member are configured to pass along an access path defined by a bronchi of the lung, wherein the elongate shaft is substantially less flexible than the elongate member;
   an energy transfer element located at a distal end of the elongate shaft; and
   wherein when the elongate shaft and the energy transfer element extend distally beyond a distal end of the elongate member, the elongate shaft is configured to flex relative to the elongate member and form an inclined angle with respect to the elongate member such that the energy transfer element contacts a wall of the cavity or passageway substantially uniformly when the access path is misaligned relative to the cavity or passageway.

2. The device of claim 1, wherein the energy transfer element is located on an expandable member capable of increasing in diameter to contact the tissue.

3. The device of claim 2, wherein the elongate shaft is adapted to restrain the expandable member in a reduced diameter configuration.

4. The device of claim 2, wherein the expandable member comprises a basket.

5. The device of claim 4, wherein the energy transfer element comprises a leg of the basket.

6. The device of claim 5, wherein the device is adapted to deliver energy with an electrode.

7. A method for treating a cavity or passageway within a body, the method comprising:
   advancing a treatment device including an elongate portion, a distal treatment portion and a junction therebetween into the cavity or passage way via an access path,
   the junction articulating to alter the orientation of the treatment portion relative to the elongate portion, so that when misalignment of the access path and the cavity or passage occur that the treatment portion is in substantially uniform contact with a wall of the cavity or passageway, wherein the cavity or passageway is within a lung, and the access path is along the bronchi.

8. The method of claim 7, wherein articulation of the junction substantially aligns the treatment portion with the cavity or passage.

9. The method of claim 7, further comprising opening the treatment portion from a closed delivery configuration to an open configuration.

10. The method of claim 9, wherein articulation of the junction occurs without substantially changing an open shape of the distal end of the device.

* * * * *

UNITED STATES PATENT AND TRADEMARK OFFICE
CERTIFICATE OF CORRECTION

| | | |
|---|---|---|
| PATENT NO. | : 7,853,331 B2 | Page 1 of 1 |
| APPLICATION NO. | : 11/420442 | |
| DATED | : December 14, 2010 | |
| INVENTOR(S) | : Gary S. Kaplan et al. | |

It is certified that error appears in the above-identified patent and that said Letters Patent is hereby corrected as shown below:

Title page, item [56] on page 4, under "Other Publications", in column 2, line 16, delete "Jerse," and insert -- Jersey, --, therefor.

Title page, item [56] on page 4, under "Other Publications", in column 2, line 31, after "filed" insert -- on --.

In column 5, line 22, delete "leur fittings)," and insert -- luer fittings), --, therefor.

In column 16, line 15, delete "leur fitting" and insert -- luer fitting --, therefor.

In column 16, line 18, delete "leur fitting" and insert -- luer fitting --, therefor.

In column 18, line 25, in Claim 7, delete "passage way" and insert -- passageway --, therefor.

Signed and Sealed this
Twelfth Day of April, 2011

David J. Kappos
*Director of the United States Patent and Trademark Office*